(12) United States Patent
Ozcan et al.

(10) Patent No.: US 9,007,433 B2
(45) Date of Patent: Apr. 14, 2015

(54) INCOHERENT LENSFREE CELL HOLOGRAPHY AND MICROSCOPY ON A CHIP

(75) Inventors: Aydogan Ozcan, Los Angeles, CA (US); Serhan Omer Isikman, Los Angeles, CA (US); Chetin Oztoprak, Venice, CA (US)

(73) Assignee: The Regents of the University of California, Oakland, CA (US)

( * ) Notice: Subject to any disclaimer, the term of this patent is extended or adjusted under 35 U.S.C. 154(b) by 308 days.

(21) Appl. No.: 13/502,725

(22) PCT Filed: Oct. 19, 2010

(86) PCT No.: PCT/US2010/053225
§ 371 (c)(1),
(2), (4) Date: Apr. 18, 2012

(87) PCT Pub. No.: WO2011/049965
PCT Pub. Date: Apr. 28, 2011

(65) Prior Publication Data
US 2012/0218379 A1    Aug. 30, 2012

Related U.S. Application Data

(60) Provisional application No. 61/253,276, filed on Oct. 20, 2009, provisional application No. 61/331,500, filed on May 5, 2010.

(51) Int. Cl.
*H04N 5/89* (2006.01)
*G03H 1/06* (2006.01)
(Continued)

(52) U.S. Cl.
CPC .............. *G03H 1/06* (2013.01); *G01N 15/1475* (2013.01); *G01N 15/1484* (2013.01);
(Continued)

(58) Field of Classification Search
CPC .................. G01N 15/1475; G01N 2015/1454; G01N 2015/1006
See application file for complete search history.

(56) References Cited

U.S. PATENT DOCUMENTS 7,431,883 B2 * 10/2008 Bell .............................. 422/67
2004/0165778 A1 * 8/2004 Cartlidge et al. ............. 382/211
(Continued)

FOREIGN PATENT DOCUMENTS

WO    2008090330 A1    7/2008

OTHER PUBLICATIONS

Hardie et al., Joint MAP Registration and High-Resolution Image Estimation Using a Sequence of Undersampled Images, IEEE, vol. 6 No. 12, Dec. 1997.
(Continued)

*Primary Examiner* — Andy Rao
*Assistant Examiner* — Tyler Edwards
(74) *Attorney, Agent, or Firm* — Vista IP Law Group LLP

(57) ABSTRACT

A system for imaging a cytological sample includes a sample holder configured to hold a cytological sample. A spatial filter is disposed at a distance $z_1$ from the sample holder on first side of the sample holder, the spatial filter having an aperture disposed therein configured to allow the passage of illumination. An imaging sensor array is disposed at a distance $z_2$ from the sample holder on a second, opposite side of the sample holder. An illumination source is configured to illuminate the cytological sample through the aperture, the spatial filter being interposed between the illumination source and the sample holder.

15 Claims, 18 Drawing Sheets

(51) Int. Cl.
*G01N 15/14* (2006.01)
*G03H 1/04* (2006.01)
*G03H 1/08* (2006.01)
*G01N 15/10* (2006.01)
*G03H 1/22* (2006.01)

(52) U.S. Cl.
CPC ............... *G01N 2015/1006* (2013.01); *G01N 2015/1454* (2013.01); *G03H 1/0443* (2013.01); *G03H 2001/0447* (2013.01); *G03H 2222/24* (2013.01); *G03H 1/0866* (2013.01); *G03H 2001/0454* (2013.01); *G03H 2001/0825* (2013.01); *G03H 2001/2284* (2013.01); *G03H 2222/13* (2013.01); *G03H 2222/22* (2013.01); *G03H 2223/18* (2013.01); *G03H 2226/11* (2013.01); *G03H 2227/02* (2013.01); *G03H 2240/62* (2013.01); *G03H 1/041* (2013.01)

(56) References Cited

U.S. PATENT DOCUMENTS

2005/0174572 A1  8/2005  Czarnek
2009/0116011 A1* 5/2009  Kenyon .................. 356/338

OTHER PUBLICATIONS

Ozcan et al., Ultra wide-filed lens-free monitoring of cells on-chip, Lab on Chip 8, 89-106, Nov. 1, 2007.
Ozcan et al., Lens-free On-Chip Cytometry for wireless Health Diagnosis, IEEE LEOS Newsletter, Oct. 2008.
Seo et al., Lensfree On-chip Cytometry Using Tunable Monochromatic Illumination and Digital Noise Reduction, Multi-color LUCAS, Sep. 2008.
Seo et al., Lensfree holographic imaging for on-chip cytometry and diagnostics, Lab on a Chip, 9, 777-787, Dec. 5, 2008.
Su et al., Towards Wireless Health: Lensless On-Chip Cytometry, Biophotonics, Dec. 2008.
Su et al., High-Throughput Lensfree Imaging and Characterization of Heterogeneous Cell Solution On a Chip, Biotechnology and Bioengineering, Sep. 8, 2008.
Isikman et al., Lensfree Cell Holography On a Chip: From Holographic Cell Signatures to Microscopic Reconstruction, LEOS Annual Meeting Conf. Proceedings, Oct. 2009.
PCT International Preliminary Report on Patentability (Chapter I of the Patent Cooperation Treaty) for PCT/US2010/053225, Applicant: The Regents of the University of California, Form PCT/IB/326 and 373, dated May 3, 2012 (7pages).
PCT International Search Report for PCT/US2010/053225, Applicant: The Regents of the University of California, Form PCT/ISA/210 and 220, dated Feb. 3, 2011 (4 pages).
PCT International Preliminary Report on Patentability (Chapter I of the Patent Cooperation Treaty) for PCT/US2010/053225, Applicant: The Regents of the University of California, Form PCT/IB/326 and 373, dated Feb. 3, 2011 (8 pages).
Office Action dated Apr. 30, 2014 in Japanese Patent Application No. 2012-535307, Applicant: The Regents of the University of California, including English Summary prepared by Kita-Aoyama International Patent Bureau (10pages).
Seo, S., Holographic LUCAS: Lensfree Ultra wide field Cell monitoring Array platform based on Shadow imaging, 2009 Annual Reseach Review, University of California, Los Angeles, Electrical Engineering Department, Apr. 24, 2009, p. 32.
Extended European Search Report dated Mar. 7, 2014 in European Patent Application No. 10825529.0-1904, Applicant: The Regents of the University of California\, (9pages).
Isikman, Serhan et al., Lensfree Cell Holography On a Chip: From Holographic Cell Signatures to Microscopic Reconstruction; LEOS 2009, 22nd Annual Meeting of the IEEE Lasers and Electro-Optics Society. Leo 2009-4-8 Oct. 2009, Belek-Antalya, Turkey, IEEE, Piscataway, NJ. USA, Oct. 4, 2009, pp. 404-405, XP031572578, ISBN: 978-1-4244-3680-4.
EPO Third Party Observations Communication pursuant to Rule 114(2) EPC dated Nov. 26, 2014 in European Application No. 10825529.0 (7 pages).
Ryle, P et al., "Digital in-line holography of biological specimens" Proc. SPIE 631, Optical Information Systems IV, 63110C (Aug. 30, 2006); doi 10.1117/12.680798 (8 pages).
Coskun, A.F. et al., Lensless wide-field fluorescent imaging on a chip using compressive decoding of sparse objects, Optics Express, vol. 18, Issue 10, pp. 10510-10523 (2010).
Dubois, F. et al., E. Partial spatial coherence effects in digital holographic microscopy with a laser source. Appl. Opt. 43, 1131-1139 (2004).
Tseng, D. et al., Lensfree microscopy on a cellphone, Lab Chip, Jul. 21, 2010 10(14):1787-92.
Xu, W. et al., Digital in-line holography for biological applications. Proc. Natl. Acad. Sci. U.S.A. 98, 11301-11305 (2001).

* cited by examiner

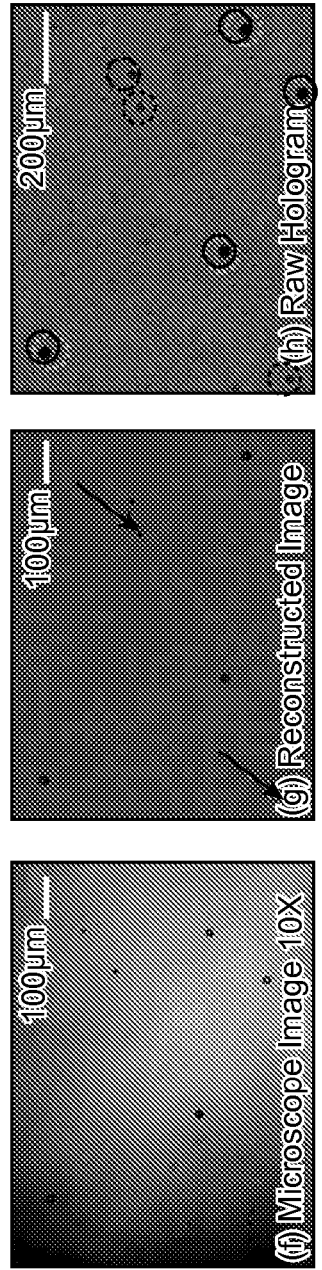
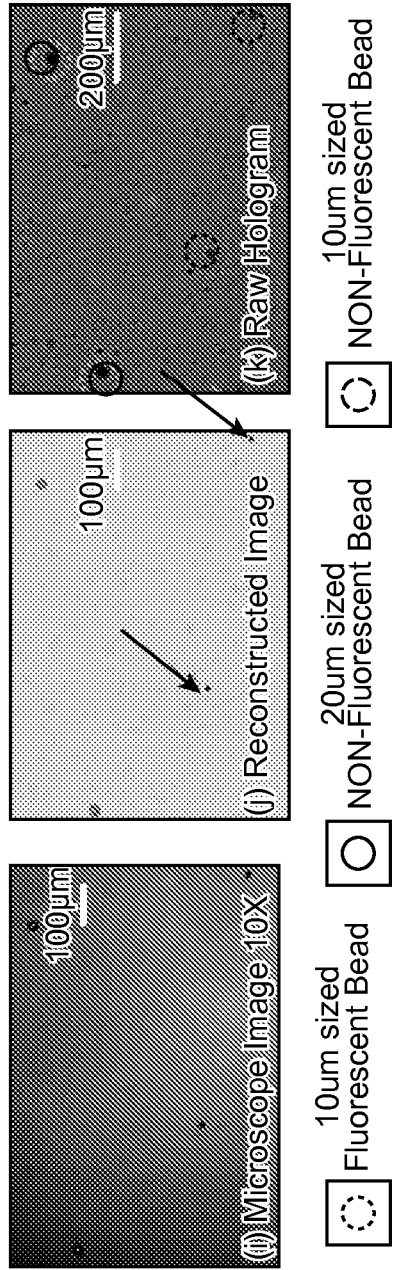
FIG. 6f — (f) Microscope Image 10X
FIG. 6g — (g) Reconstructed Image
FIG. 6h — (h) Raw Hologram
FIG. 6i — (i) Microscope Image 10X
FIG. 6j — (j) Reconstructed Image
FIG. 6k — (k) Raw Hologram
10um sized Fluorescent Bead
10um sized NON-Fluorescent Bead
20um sized NON-Fluorescent Bead

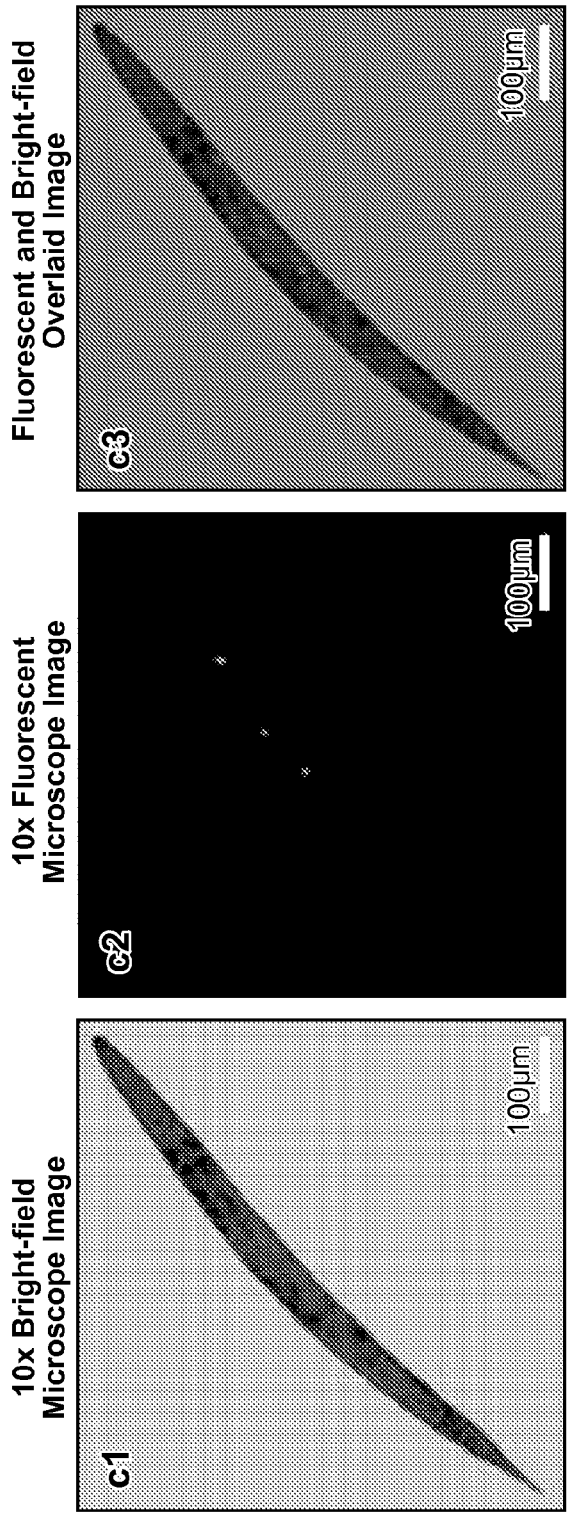
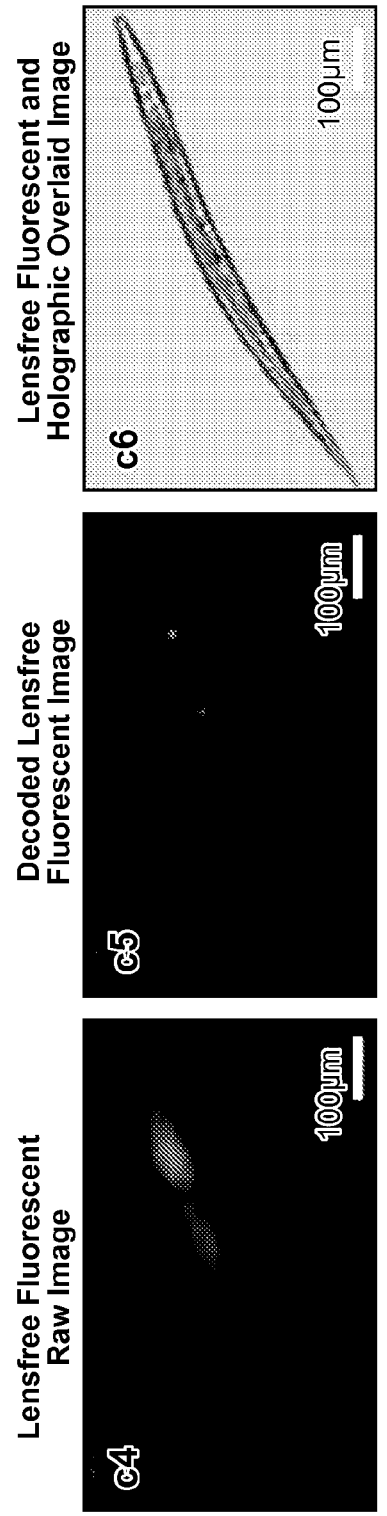
FIG. 7(c1) 10x Bright-field Microscope Image
FIG. 7(c2) 10x Fluorescent Microscope Image
FIG. 7(c3) Fluorescent and Bright-field Overlaid Image
FIG. 7(c4) Lensfree Fluorescent Raw Image
FIG. 7(c5) Decoded Lensfree Fluorescent Image
FIG. 7(c6) Lensfree Fluorescent and Holographic Overlaid Image

INCOHERENT LENSFREE CELL HOLOGRAPHY AND MICROSCOPY ON A CHIP

RELATED APPLICATIONS

This Application is a U.S. National Stage filing under 35 U.S.C. §371 of International Application No. PCT/US2010/053225, filed Oct. 19, 2010, which claims priority to U.S. Provisional Patent Application No. 61/253,276, filed on Oct. 20, 2009 and U.S. Provisional Patent Application No. 61/331,500, filed on May 5, 2010. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

FIELD OF THE INVENTION

The field of the invention generally relates to imaging systems and methods and more particularly imaging systems that have particular application in the imaging and analysis of small particles such as cells, organelles, cellular particles and the like.

BACKGROUND

For decades optical microscopy has been the workhorse of various fields including engineering, physical sciences, medicine and biology. Despite its long history, until relatively recently, there has not been a significant change in the design and working principles of optical microscopes. Over the last decade, motivated partially by the quest to better understand the realm of the nano-world, super-resolution techniques started a renaissance for optical microscopy by addressing some of the most fundamental limitations of optical imaging such as the diffraction limit. Besides these super-resolution techniques, several other novel imaging architectures were also implemented to improve the state of the art in optical microscopy towards better speed, signal to noise ratio (SNR), contrast, throughput, specificity, etc. This recent progress in microscopy utilized various innovative technologies to overcome the fundamental barriers in imaging and has created significant excitement in a diverse set of fields by enabling new discoveries to be made.

However, together with this progress, the overall complexity and the cost of the optical imaging platforms has increased. Expensive and sometimes large optical imaging systems often limit the widespread use of some of these advanced optical imaging modalities beyond well-equipped laboratories.

In the meantime, a rapid advancement in digital technologies has occurred, with much cheaper two-dimensional solid state detector arrays having significantly larger areas with smaller pixels, better dynamic ranges, frame rates and signal to noise ratios, as well as much faster, cheaper and more powerful digital processors and memories. This on-going digital revolution, when combined with advanced imaging theories and numerical algorithms, also creates an opportunity for optical imaging and microscopy to face another dimension in this renaissance towards simplification of the optical imaging apparatus, making it significantly more compact, cost-effective and easy to use, potentially without a trade-off in its performance.

Lenses for decades have been helping detectors (analog or digital) to operate at the lowest possible space-bandwidth product that is determined by the desired field-of-view and the resolution of the image. However, the above discussed digital revolution has already advanced the state of the art for digital imagers such that a 2D space-bandwidth product of >10-20 Million is readily available nowadays. This implies that today's detector arrays are now much better suited to handle the information distortion caused by diffraction, which may then raise questions on the absolute necessity of the use of lenses in optical imaging. Moreover, today's digital processors together with novel algorithms are also in much better shape to process, almost instantaneously, the acquired information at the detector end for taking the job of a physical lens. Looking at this picture, one can conclude that the widespread use of lenses (or similar wavefront shaping elements) in optical imaging can now be potentially replaced for several application needs (specifically for cell microscopy) by cost-effective, compact and much simpler optical architectures that compensate in the digital domain for the lack of complexity of optical components. This approach should especially address the needs and the requirements of resource limited settings, potentially providing a leapfrog in the fight against various global health related problems involving infectious diseases.

Quite importantly, microscopy in resource-limited settings has requirements considerably different from those of advanced laboratories, and such imaging devices should be simple to use and operate, cost-effective, compact, and light-weight, while at the same time being properly accurate. Another field that would enormously benefit from lensfree, compact and cost-effective on-chip digital imagers is the field of microfluidics. Over the last decade, microfluidics has revolutionized the available toolset to handle cells by significantly reducing the required device and reagent volumes as well as the associated costs. This has, in some instances, enabled so-called lab-on-a-chip applications. Despite all the progress that has occurred on merging optical technologies with microfluidics, one area that still remains relatively low-throughput, bulky and costly is the integration of optical microscopy platforms with microfluidic features found on such devices. Without significant miniaturization and simplification of this imaging platform together with an increase in throughput, the true extent of the microfluidic revolution cannot be fully realized especially for cytometry applications.

The fruits of this thinking have already appeared in the literature, where various lensfree on-chip imaging architectures were successfully demonstrated. See e.g., Xu, W., Jericho, M. H., Meinertzhagen, I. A. & Kruezer, H. J. Digital in-line holography for biological applications. Proc. Natl. Acad. Sci. U.S.A. 98, 11301-11305 (2001). Among these approaches, lensfree digital holography deserves a special attention since with new computational algorithms and mathematical models, it has the potential to make the most out of this digital revolution. In this context, lensfree digital in-line holography has already been successfully demonstrated for high-resolution microscopy of cells and other micro-organisms as described in Xu et al. above. Conventional coherent lensfree in-line holography approaches, however, demand near-perfect spatial coherence for illumination, and therefore require focusing of a laser light on a small aperture that is sized on the order of a wavelength for spatial filtering. The use of a small aperture size (e.g., 1-2 μm) requires a mechanically stable and a carefully aligned system together with a focusing lens to efficiently couple the laser radiation to the aperture for improved light throughput. This can require a robust system to ensure properly optical alignment and mechanical stability. In addition, keeping such a small aperture clean and operational over an extended period of time can be another challenge especially for uses outside the laboratory environment.

Further, in conventional lensfree in-line holography the cells of interest are typically positioned far away (e.g., >1-2 cm) from the sensor surface such that the holographic signature of each cell is spread substantially over the entire sensor area, where all the cells' particular holographic "signatures" significantly overlap. Such an approach unfortunately limits the imaging field-of-view (FOV) at the cell plane. All these requirements increase the cost and the size of the optical instrument. Further, these constraints also make conventional lensfree coherent in-line holography approaches inconvenient for use in resource-limited settings such as in the field.

Incoherent or partially coherent sources in holography have also been utilized in different lens-based optical architectures. These holographic imaging techniques are not, however, classified as "on-chip" as they utilize various bulky optical components and therefore they can be considered under the same category as the advanced imaging modalities discussed above making them much less suitable for uses outside a laboratory. Much simpler approaches using partially coherent lensfree in-line holography have also been recently demonstrated for imaging of latex particles, but these techniques also suffer from a small field-of-view as they position the objects-of-interest far away from the sensor surface. See e.g., Dubois, F., Requena, M. N., Minetti, C., Monnom, O. & Istasse, E. Partial spatial coherence effects in digital holographic microscopy with a laser source. Appl. Opt. 43, 1131-1139 (2004). Further, these studies used coupling optics for the illumination such as a microscope objective-lens and had relatively coarse imaging performance.

SUMMARY

In one aspect of the invention, an alternative incoherent cell holography and microscopy platform is disclosed that utilizes cost-effective and compact optical components to enable digital recognition and microscopic imaging of cells or multicellular organisms. The platform and method enables sub-cellular resolution over a large field-of-view without the need for any lenses (although lenses could be incorporated), coherent sources such as lasers, or any other bulky optical components. With this lensless system, one can record individual phase and amplitude holograms of various cell types for subsequent digital recognition and automated counting of each cell type based on their 2D holographic signatures. Further the system and method enables one to accurately reconstruct microscopic images featuring sub-cellular resolution over a large field-of-view even at cell densities reaching up to about 0.4 Million cells/µL. Because this platform utilizes a simple, compact, light-weight and cost-effective optical components that are tolerant to misalignment, it may also provide an important tool for cell biology, microfluidics and telemedicine based cytometry applications in resource-poor settings. For instance, the platform may be integrated into a relatively small device that can be used for the diagnosis and investigation of various infectious diseases such as malaria, HIV, and tuberculosis. The device may also be able to screen water for disease-causing parasites or other infectious diseases.

Toward this end, the performance of the incoherent lensless cell holography platform is demonstrated for automated counting and microscopic imaging of whole blood cells with a spatial resolution sufficient to differentiate granulocytes, monocytes and lymphocytes from each other with minimal sample preparation steps.

There are several aspects of this lensless incoherent cell holography platform that makes it highly advantageous for cell biology in microfluidic systems and for cytometry applications. First, the light source in this holographic approach does not need to be a laser. Rather, a completely incoherent source can be used without the need for any lenses or other bulky optical components. This feature greatly simplifies the optical set-up, making it cost-effective and compact, as well as eliminating the coherent speckle noise and substrate induced multiple-reflection interference effects in cell holograms. Second, the lensless incoherent cell holography approach does not require a small aperture size for illumination and therefore improves the light throughput of the imaging system by orders-of-magnitude without causing an issue for cell hologram pattern analysis or digital image reconstruction. The large aperture size (e.g., 50-100 µm) also eliminates the use of any coupling/focusing optics between the source and the aperture planes, unlike most conventional holography approaches. This feature makes it robust to mechanical misalignments or potential clogging problems. This enables long operational times without imaging artifacts or the need for realignment, making it highly suitable for filed use. Third, because the cells of interest are placed much closer to the sensor array than to the light source (with a fringe magnification of ~1), one can image a much larger field-of-view typically by >10 fold than an optical microscope or >50-100 fold than a conventional lensless in-line holographic microscope.

This property also permits simultaneous on-chip detection of fluorescent signals over a large field of view without the need for any lenses or expensive thin-film fluorescent filters, which is highly important to create a hybrid on-chip imaging platform that is capable of merging incoherent holographic microscopy with fluorescent detection to increase the specificity and functionality of the lensfree imaging platform. Finally, apart from reconstructing microscopic images of cells through holographic processing of the embedded optical phase, the system can also detect a unique two dimensional holographic texture (i.e., a fingerprint) corresponding to each cell, which provides an alternative source of information that complements the reconstructed cell images. Through pattern and/or texture analysis of such holographic cell signatures (both phase and amplitude) it is possible to recognize the type and the state of each cell of interest (without digital reconstruction), which is especially important for cytometry applications. For instance, observed hologram signatures may enable very rapid diagnostic decisions (e.g., comparison of hologram signatures of healthy vs. diseased cells). The lensfree holographic imaging system and method described herein can be combined with digital electronics to provide a transformative solution to some of the unmet needs of cell biology, cytometry, and medical diagnostics, especially for resource-limited environments.

In one embodiment of the invention, a system for imaging a cytological sample includes a sample holder configured to hold a cytological sample and a spatial filter disposed at a distance $z_1$ from the sample holder on first side of the sample holder, the spatial filter having an aperture disposed therein configured to allow the passage of illumination. The system further includes an imaging sensor array disposed at a distance $z_2$ from the sample holder on a second, opposite side of the sample holder and an illumination source configured to illuminate the cytological sample through the aperture, the spatial filter being interposed between the illumination source and the sample holder.

In still another aspect of the invention, the system may further include a prism interposed between the spatial filter and the sample holder and a fluorescent illumination source configured to illuminate the cytological sample through the prism, wherein substantially all of the incident fluorescent illumination is reflected through total internal reflection (TIR). The incident fluorescent illumination may be from the side or at an angle while the holographic illumination source is directed from the top down. Fluorescent emissions from one or more species in the sample may be detected by the imaging sensor array.

In yet another aspect of the invention, a method of imaging a cytological sample includes illuminating a front side of a sample holder configured to hold a cytological sample with an illumination source emitting at least partially incoherent light, the at least partially incoherent light passing through an aperture prior to illuminating the cytological sample. One or more image frames are obtained from an imaging sensor array located on or adjacent to a back side of the sample holder.

In still another aspect of the invention, a portable system for imaging a cytological sample includes a mobile communications device having sample holder configured to hold a cytological sample, the mobile communications device dimensioned for hand-held portability. The portable system includes a spatial filter disposed at a distance $z_1$ from the sample holder on first side of the sample holder, the spatial filter having an aperture disposed therein configured to allow the passage of illumination and an imaging sensor array located in the mobile communications device and disposed at a distance $z_2$ from the sample holder on a second, opposite side of the sample holder. The portable system includes an illumination source configured to illuminate the cytological sample through the aperture, the spatial filter being interposed between the illumination source and the sample holder. The mobile communications device may include a mobile phone or personal digital assistant (PDA) or the like.

BRIEF DESCRIPTION OF THE DRAWINGS

FIGS. 6(a)-6(k) illustrates lensfree holographic and fluorescent imaging of the same field of view that is obtained sequentially for a heterogeneous solution containing fluorescent and non-fluorescent beads.

DETAILED DESCRIPTION OF THE ILLUSTRATED EMBODIMENTS

Figure 1:
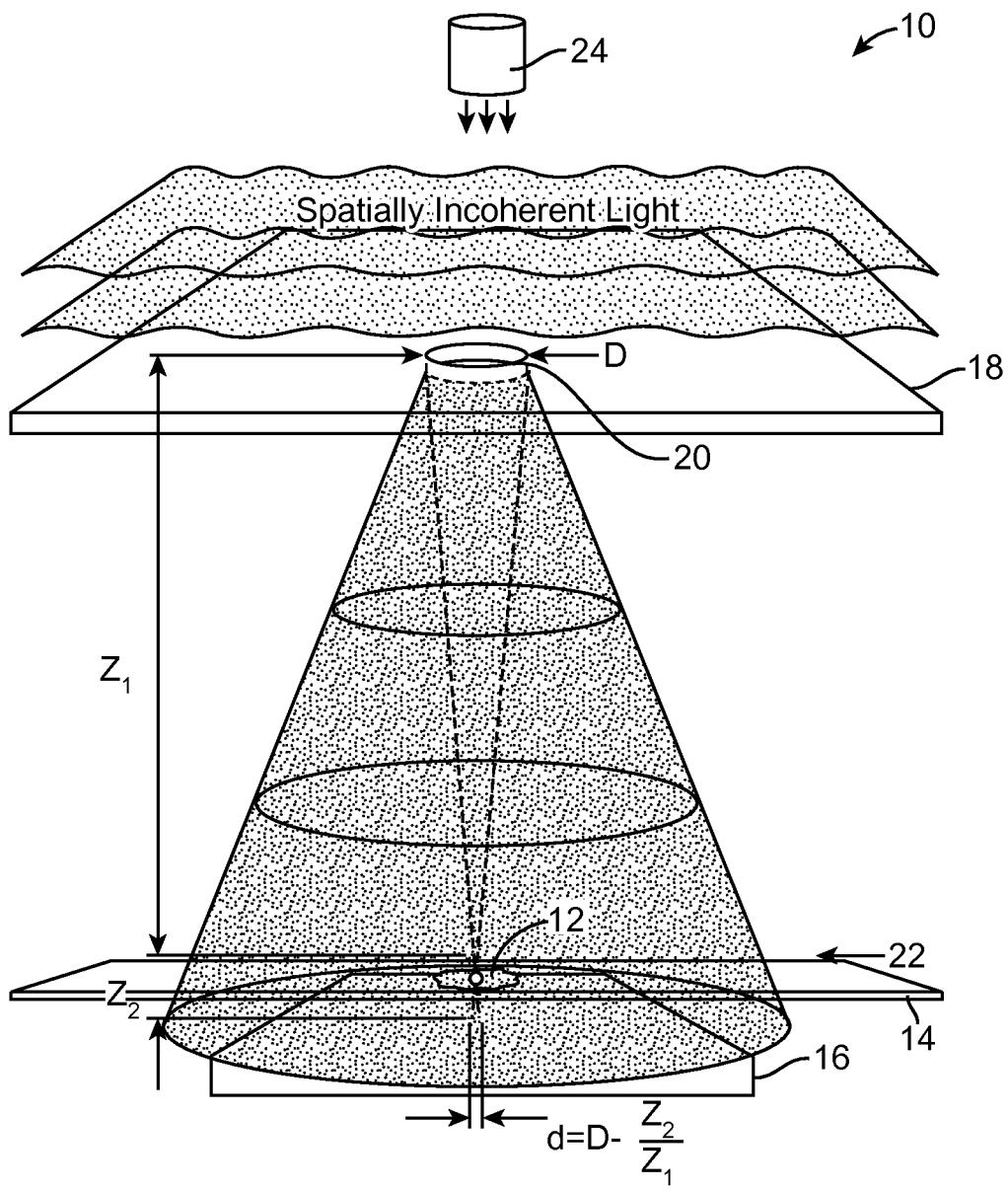
FIG. 1 is a schematic representation of an incoherent lensfree cell holography and microscopy system according to one embodiment.

FIG. 1 illustrates a system 10 for imaging a cytological sample 12 according to one embodiment. The system includes a sample holder 14 that is configured to hold a cytological sample 12. The sample holder 14 may include a glass or plastic slide (with or without cover slip), container, cuvette, or the like. The sample holder 14 is preferably made from an optically transparent material at least at the wavelengths of light in which the system 10 operates. The cytological sample 12 contains biological elements that are to be imaged, namely, cells or cellular features. The sample 12 may include blood, sweat, sputum, mucus, or even environmental samples (e.g., water from a lake or stream). The cytological sample 12 may be a prepared sample or it may a direct biological sample that is placed on the sample holder 14 without preparation. For example, in the case of red blood cells as the sample, a blood sample may be diluted with either 1× phosphate buffered solution (PBS) or Blood Bank Saline (e.g., Fisherbrand, Blood Bank Saline, Fisher Scientific).

The sample holder 14 is positioned above an imaging sensor array 16. That is to say the imaging sensor array 16 is located adjacent to the back side of the sample holder 14. The surface of imaging sensor array 16 may be in contact with or close proximity to the back side of the sample holder 14. The imaging sensor array 16 may comprise, for example, a charged coupled device (CCD) or a complementary metal-oxide semiconductor (CMOS). The imaging sensor array 16 may be monochromatic or color. The imaging sensor array 16 generally has a small pixel size which is less than 9.0 µm in size and more particularly, smaller than 5.0 µm in size (e.g., 2.2 µm or smaller). Generally, sensors having smaller pixel size will produce higher resolutions. One benefit of the imaging method described herein is that a spatial resolution better than pixel size can be obtained.

Still referring to FIG. 1 the system 10 includes a spatial filter 18 that disposed away from the top surface of the sample holder 14. The spatial filter 18 has an aperture 20 contained therein that is configured to permit the passage of illumination. The aperture 20 has a diameter (D) that is typically in the range of 50 μm to about 100 μm. FIG. 1 illustrates a cell plane 22 that represents a plane that intersects the biological elements (e.g., cells) contained in the sample 12. This cell plane 22 is generally disposed substantially at the surface of the sample holder 14 that contains the cytological sample. As seen in FIG. 1, the spatial filter 18 is located at a distance $z_1$ from the cell plane 22. The imaging plane of the imaging sensor array 16 is located at a distance $z_2$ from the cell plane 22. In the system 10 described herein, $z_2 \ll z_1$. For example, the distance $z_1$ may be on the order of around 1 cm to around 10 cm. In other embodiments, the range may be smaller, for example, between around 5 cm to around 10 cm. The distance $z_2$ may be on the order of around 0.05 mm to 2 cm, however, in other embodiments this distance $z_2$ may be between around 1 mm to 2 mm.

Figure 2:
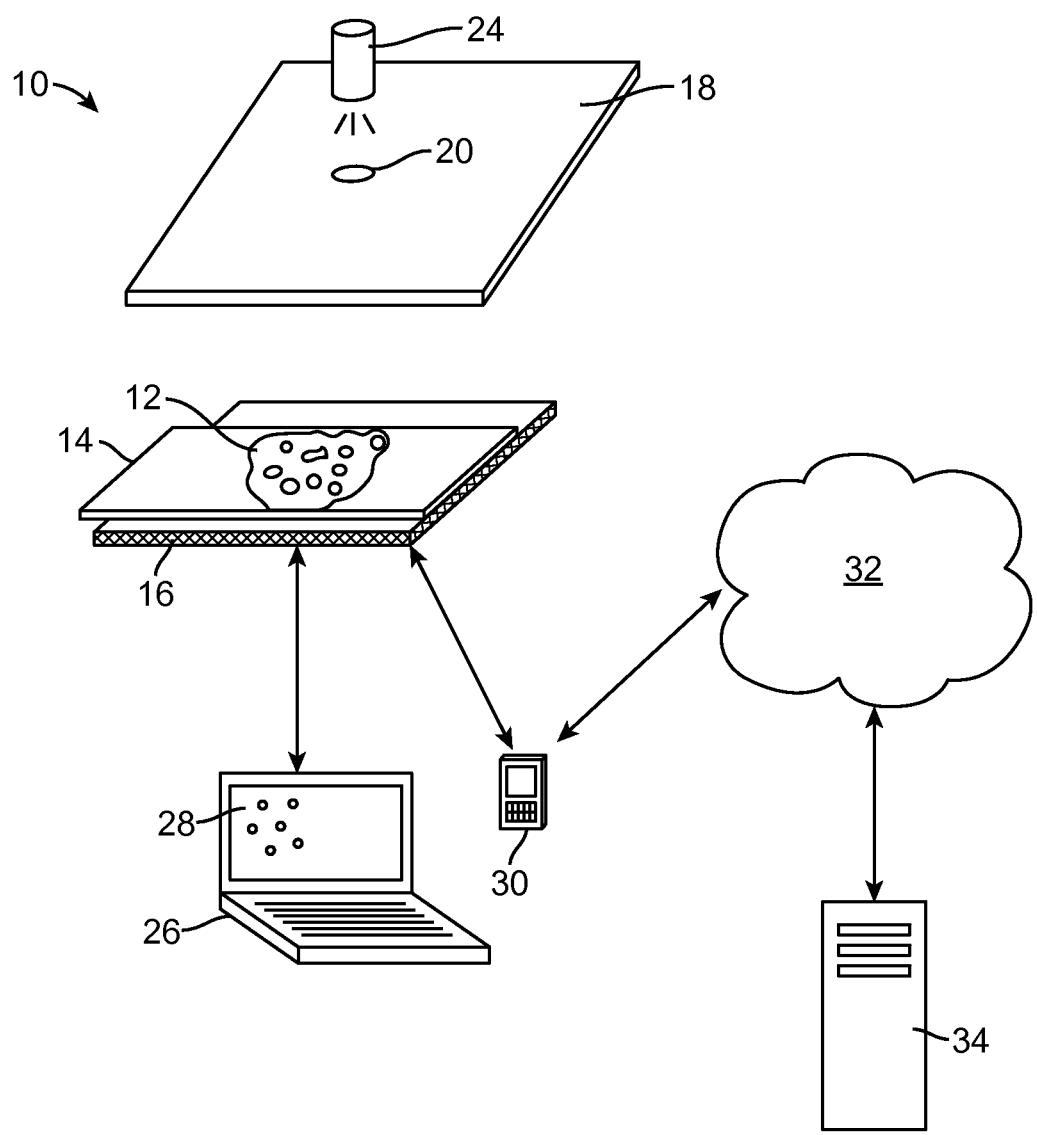
FIG. 2 is a schematic representation of components of incoherent lensfree cell holography and microscopy system according to one embodiment.

The system 10 includes an illumination source 24 as illustrated in FIG. 2. The illumination source 24 is preferably an incoherent or partially incoherent light source. Light emitting diodes (LEDs) are one example of a light source 24 that can be used as the illumination source 24. LEDs are relative inexpensive, durable, and have generally low power requirements. One of the significant advantages of the system 10 is that the design allows from some variance in the mechanical tolerances such that the system 10 still operates even if there is not perfect alignment between the illumination source 24, spatial filter 18, and the imaging sensor array 16.

FIG. 2 illustrates the system 10 in conjunction several additional components. In one embodiment, a computer 26 such as a laptop, desktop, or the like is operatively connected to the system 10 such that images (e.g., image frames) are transferred from the imaging sensor array 16 to the computer 26 for data acquisition and image processing. The computer 26 includes one or more processors (not shown) that, as described herein in more detail, runs software that acquires an image of the sample 12 that includes the holographic amplitude or intensity. The software on the computer 26 then recovers the lost phase of the image. Having both the holographic amplitude and recovered phase of the same image, the software then reconstructs an image of the sample 12. This reconstructed image 12 can be displayed to the user on, for example, a display 28 or the like. The software may also identify and display particular cells of interest based on their holographic signature. For example, software may be programmed to identify lymphocytes in the sample while ignoring granulocytes and monocytes. These lymphocytes, which are identified by their unique holographic signature, are then displayed for the user on the display 28. The software may also count cell populations or cell sub-populations which information can also be displayed on the display 28. The unique holographic signature may also be used to identify disease states. For instance, red blood cells RBCs may be evaluated by the software to look for a disease state such as sickle cell anemia or infection with malaria. This information can be reported back to the user via the display 28.

In another alternative embodiment, a mobile communications device 30 is operatively connected to the system 10. The images (e.g., image frames) may be transferred from the imaging sensor array 16 to the mobile communications device 30 for data acquisition and image processing using one or more processors contained in the mobile communications device 30. Alternatively, the mobile communication device 30 may simply transfer data over a communications network 32 which is then transferred to a remote computer 34 for further processing. The communications network 32 may include, for example, a wide area network such as the Internet or may include wireless network that is employed to transmit and receive data in conventional mobile communications devices 30. Data may be sent back to the mobile communications device 30 using the same communications network 32.

In yet another alternative embodiment, as explained in more detail below, the system components are integrated into the mobile communications device 30. Namely, the mobile communications device 30 includes the imaging sensor array 16, illumination source 24, spatial filter 18, and is configured to receive the sample holder 14 for analysis using the mobile communications device 30. In this embodiment, one or more processors contained in the mobile communication device 30 contain the software for image analysis and processing. Alternatively, the mobile communication device 30 may simply transfer the raw image files over a communications network 32 where a remote computer 34 is used to image processing and analysis. Results can then be sent back to the mobile communication device 30 via the communications network 32.

In still another embodiment, the illumination source 24, spatial filter 18, and imaging sensor array 16 may be contained in a self-contained unit that is configured to receive a sample holder 14. The self-contained unit may be connected to a computer 26 through a wired (e.g., USB) or wireless (e.g., Bluetooth) connection. Alternatively, the self-contained unit by be connected to a mobile communications device 30 via a similar wired or wireless connection.

Figure 3:
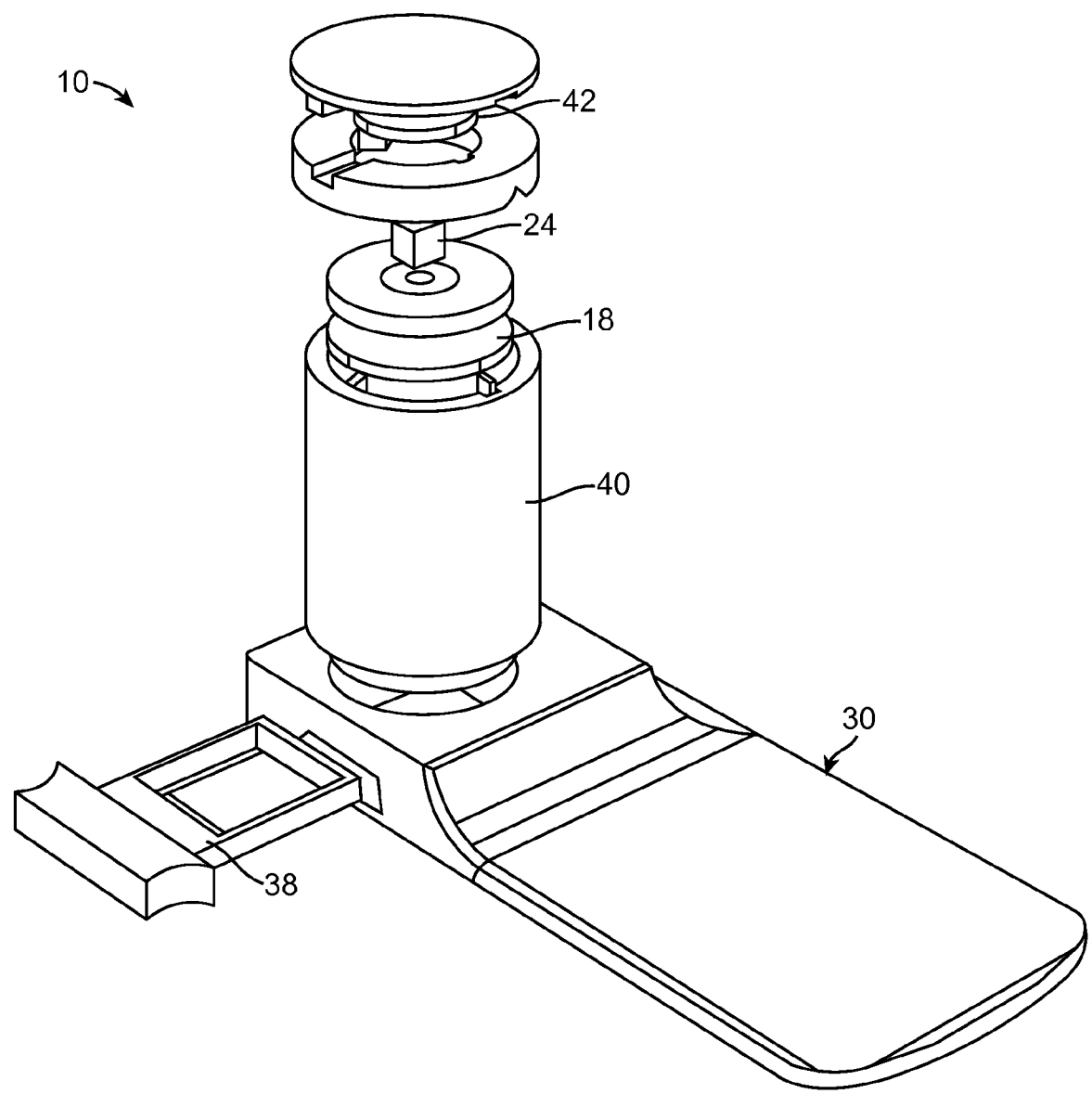
FIG. 3 is a partially exploded view of a mobile communication device having therein integrated incoherent lensfree cell holography functionality.

FIG. 3 illustrates an embodiment of a system 10 in which the lensfree holographic imaging system is integrated with a mobile communications device 30. The mobile communication device 30 may include a mobile phone, personal digital assistant (PDA), or other portable electronic device. The mobile communications device 30 preferably has wireless functionality such that images, data, and results may be transmitted remotely to an offsite location through a communication network 32. Such wireless transmission may occur over conventional wireless spectrums and data protocols used to carry data (e.g., CDMA networks, GSM networks or the like). Data may also be transmitted to another computer or similar device via other shorter-range wireless protocols such as Bluetooth, WiFi or the like.

The imaging sensor array 16 (not shown in FIG. 3) is located within the mobile communication device 30. The imaging sensor array 16 may include the same imaging hardware used to take pictures or movies in such devices (e.g., CMOS, CCD, or equivalent). Alternatively, the imaging sensor array 16 may be specialized component produced specifically for holographic imaging applications. As seen in FIG. 3, the mobile communication device 30 includes a sample loader 38 that is configured to hold the sample holder 14. For example, the sample loader 38 may be moveable into an open position as illustrated in FIG. 3 in which the sample holder 14 is positioned into the sample loader 38. The sample loader 38 is then moved into a closed position whereby the sample holder 14 with the sample 12 is positioned into position over the imaging sensor array 16. Alternatively, in another embodiment, the sample holder 14 (e.g., slide, cuvette, or the like) may be inserted directly into the mobile communication device 30 without the aid of a sample loader 38. In either case, the sample 12 is placed directly on or above the imaging sensor array 16 such that cell plane 22 is close to the detector plane. An optically transparent layer (not shown) above the imaging sensor array 16 may fix this distance.

Still referring to FIG. 3, the system 10 includes an extension or housing 40 that is configured to contain the illumination source 24 along with the spatial filter 18. The extension 40 may be in the shape of tubular housing or the like although other shapes and geometries may be used. The extension 40 may be permanently affixed to the mobile communication device 30 or, alternatively, the extension 40 may be modular and selectively attached/detached from the mobile communication device 30. In some embodiments, the length of the extension 40 may be adjustable. The illumination source 24 is preferably an incoherent or partially incoherent light source such as a LED as illustrated in FIG. 3. The illumination source 24 may be driven or powered by the internal battery of the mobile communication device 30 or, alternatively, the extension 40 may contain the battery 42 and/or driving circuitry needed to power the illumination source 24. In still another alternative, the power source from a local computer such as computer 26 of FIG. 2 may provide the power source to run the illumination source 24 (e.g., via a USB cable or the like).

The extension 40 further includes the spatial filter 18 which contains the aperture 20 therein. As explained herein, a main advantage of the current system 10 is that the design allows for some variance in mechanical tolerances such that the imaging system can still operate even if there is not perfect alignment between the illumination source 24, spatial filter 18, and imaging sensor array 16. Thus, the system can still operate and provide images even if the mobile communication device 30 undergoes significant mechanical interruptions as one would expect with such a device 30 in the field.

The extension 40 has a length that generally places the aperture 20 some distance away (i.e., $z_1$) from the cell plane 22. Generally the distance between the cell plane 22 and the aperture 20 is in the range of about 1 cm to about 10 cm. Of course, this distance may vary beyond this range. This relatively small distance still enables the mobile communications device 30 to be hand-held and portable even when the extension 40 is attached or otherwise secured to the mobile communications device 30. The distance between the cell plane 22 and the image sensor array 16 is easily accommodated within the mobile communication device 30 but generally falls within the range of between 0.05 mm to 2 cm.

As explained above, the extension 40 may be a modular component that can be swapped-out or exchanged to provide, for example, alternative illumination sources 24. For example, one extension 40 may contain a LED of a certain color while other extensions could contain different color LEDs. These various extensions 40 could also vary in length to provide different imaging characteristics. These extensions 40 could be carried in the field as part of an imaging kit. Alternatively, a single extension 40 can contain multiple illumination sources 24 (e.g., more than one color of LEDs). These LEDs could be powered individually or together at the same time. Because a single extension 40 may also contain multiple LED configurations (of the same color or different colors) all of the sources can be turned on at the same time for imaging, or alternatively, each illumination source 24 can be turned on sequentially, while the imaging sensor array 16 is capturing holograms of the sample 12 as a function of time. Different combinations of these multiple illumination sources 24 can be turned on to create multiple holograms of the same imaging field.

In use, the sample 12 is placed above the imaging sensor array 16. The sample 12 may be loaded onto or into the sample holder 14 such as a microscope slide or a microfluidic device holding a sample such as whole blood, urine, sweat, saliva etc. The sample holder 14 is then inserted into the mobile communication device 30 either directly or through the use of a separate sample loader 38. Alternatively, the sample 12 may be directly dropped (e.g., using a dropper or pipette or the like) above the imaging sensor array 16.

The illumination source 24 is turned on and one or more image frames of the sample 12 are captured with the imaging sensor array 16. In one aspect of the invention, the processor(s) of the mobile communication device 30 can run the imaging software used for image processing and analysis. Alternatively, a USB or other known connection (e.g., Bluetooth) can be used to run the imaging software via a separate computer or the like (e.g., computer 26). In this regard, image processing can take place either on the mobile communication device 30 or off the mobile communication device 30 in a separate computer (e.g., local computer 26 or remote computer 34 in FIG. 2). For instance, raw image data could be communicated wirelessly via a communications network 32 to another remote computer 34 which could then process the images. Results could then be relayed back to the mobile communications device 30 via the same wireless communications network 32. Alternatively, the wireless communication device 30 may be self-contained and able to process images and report results directly to the user.

A wireless communication device 30 having a lensfree holographic imaging system 10 integrated therein remains lightweight yet portable. The additional imaging components added to the mobile communications device 30 typically adds only a modest amount of additional weight, in some instances less than 40 grams. Generally such a device provides an imaging field of view (FOV) that is large. Typically the achievable FOV is >24 mm$^2$, which is >10 fold larger than an optical microscope. Because the system 10 uses cost-effective, compact and components tolerant of misalignment, it offers a transformative solution for microscopy, cytometry and medical diagnostic needs, particularly so in resource-poor settings.

In the system 10, the illumination source 24 passes light through the aperture 20 of the spatial filter 18. This spatially filtered LED light, after travelling in air a distance that is typically several centimeters, interacts with the sample 12, where each cell/particle within the sample 12 scatters and refracts the incoming LED light based on its size, 3D morphology, sub-cellular elements, and refractive index. The interference of the light waves that passed through the cells with the unscattered LED light creates the hologram of each cell, which is detected using the imaging sensor array 16. The lensfree hologram of each cell is extremely rich and permits rapid reconstruction of its microscopic image through digital processing.

In one aspect, the image sensor array 16 that is used is a color-based image sensor that is installed or manufactured with the mobile communication device 30. A color-based image sensor array 16, unlike a monochrome one, has color filters at each pixel yielding what is known as the Bayer pattern composed of a periodic array of red-green-blue (RBG) pixels. In a regular lensfree holographic microscope, a color sensor would hardly be the optimal choice, since not all the pixels would receive enough light under quasi-monochromatic illumination (e.g., ~587 nm). To handle this issue of hologram distortion due to the Bayer pattern of the image, the digital image reconstruction process involves an extra step of converting the raw format (Bayer Pattern Image) into a monochrome equivalent image before conducting holographic reconstruction of the images of the cells or particles.

A digital color image is represented as an array of pixels, with each pixel represented by a mixture of primary colors. The standard primary colors used by most of the consumer cameras are Red, Green and Blue (RGB). In an ideal case, these colors can be recorded separately by splitting the light beam onto three different sensors, each recording one color. However, for cost reasons, cameras in mobile communication devices 30 typically use a single image sensor chip which is covered by a Color Filter Array (CFA) designed in a variety of patterns. The most widely used CFA pattern in image acquisition industry is called Bayer pattern which employs a repeating 2×2 pattern consisting of one Blue, one Red and two Green filters. Therefore, the raw output of a image sensor array 16 using Bayer Pattern CFA, which is usually called the Bayer Pattern Image, is made of pixels which carry information regarding one of the three primary channels. The process of merging these three channels in order to obtain a full-color image is called demosaicing.

There is an ample amount of literature on different methods for demosaicing each of which answers the needs of different applications. However, for the purpose of holographic cell phone microscopy, such standard demosaicing algorithms would generally wash out high frequency amplitude oscillations which are needed in the holographic reconstruction process. Therefore, the usage of the recorded information in its most pure format has a significant advantage of preventing any undesired artifacts that might be introduced by conventional demosaicing algorithms. For preserving the holographic diffraction signatures of microscopic objects, a demosaicing algorithm has been developed to obtain grayscale images with least distortion to the acquired holographic patterns. Unlike conventional demosaicing algorithms where it is aimed to output an RGB image by interpolating missing channels at each pixel while preserving inter-pixel as well as inter-channel correlation, the main aim of this demosaicing algorithm was to maximize spatial correlation. Therefore, the raw output of the mobile communication device 30 is treated as a monochrome image which has patterned artifacts to be ameliorated.

For a lensfree holographic pattern sampled by a color-sensor, the illumination wavelength is quite important in assuring an optimal spatial sampling performance. As explained above, 50% of the pixels on a color sensor which uses Bayer Pattern CFA are responsive to green, 25% to blue and 25% to red. Because it is desired to have as many unsaturated pixels above noise level as possible, the wavelength of illumination source 24 (e.g., LED) is selected to be in a band where both red and green pixels have high detection efficiency. Therefore, an LED at ~587 nm was used have decent performance for the red and green channels.

However, under this quasi-monochromatic illumination, the resulting raw holographic image at the color-sensor mainly suffers from two artifacts. First, even though red and green channels carry information with high signal to noise ratio, they are not equally illuminated and therefore equalization needs to be carried out between the values belonging to these two channels. Second, as a result of selecting a wavelength at which blue pixels are not sensitive enough, the third channel (blue) is highly corrupted by the noise. Hence it is required to predict all the blue pixels using neighboring green and red pixels.

The detection imbalance between the intensity levels of green and red channels is compensated using a background image acquired with identical illumination conditions that were used for capture of lensfree holograms of the objects. This background image provides a normalization coefficient matrix which determines the scaling factor for each pixel on the holographic image. This method not only equalizes the green and red channels, but also compensates for any potential artifact caused by non-uniform illumination at the sensor plane.

Once this channel equalization step is done, the remaining problem is the prediction of the missing blue channel. The approach for interpolation of the blue pixels includes an estimation step, which is done by using an edge-aware interpolation, followed by a refinement step which improves this initial prediction iteratively by using the phase recovery method (described below) that has been adapted for reconstruction of lensfree holographic images.

When a larger block of 3×3 pixels is considered, this missing channel prediction problem may also be interpreted as estimation of a missing pixel (blue) that is surrounded by eight known pixels (red and green). The simplest way to estimate this unknown pixel is straight-forward averaging of all the eight neighboring pixels. However, such an approach would oversee high frequency changes in the lensfree hologram. Instead, an edge-aware interpolation algorithm was used which adjusts the estimation of the missing pixels based on the magnitudes of the spatial derivatives in each of the four directions. Additional details of algorithm may be seen in the publication entitled "Lensfree Microscopy on Cellphone," by Tseng et al., Lab Chip, 2010 Jul. 21, 10(14):1787-92, which is incorporated by reference as if set forth fully herein.

Figure 4:
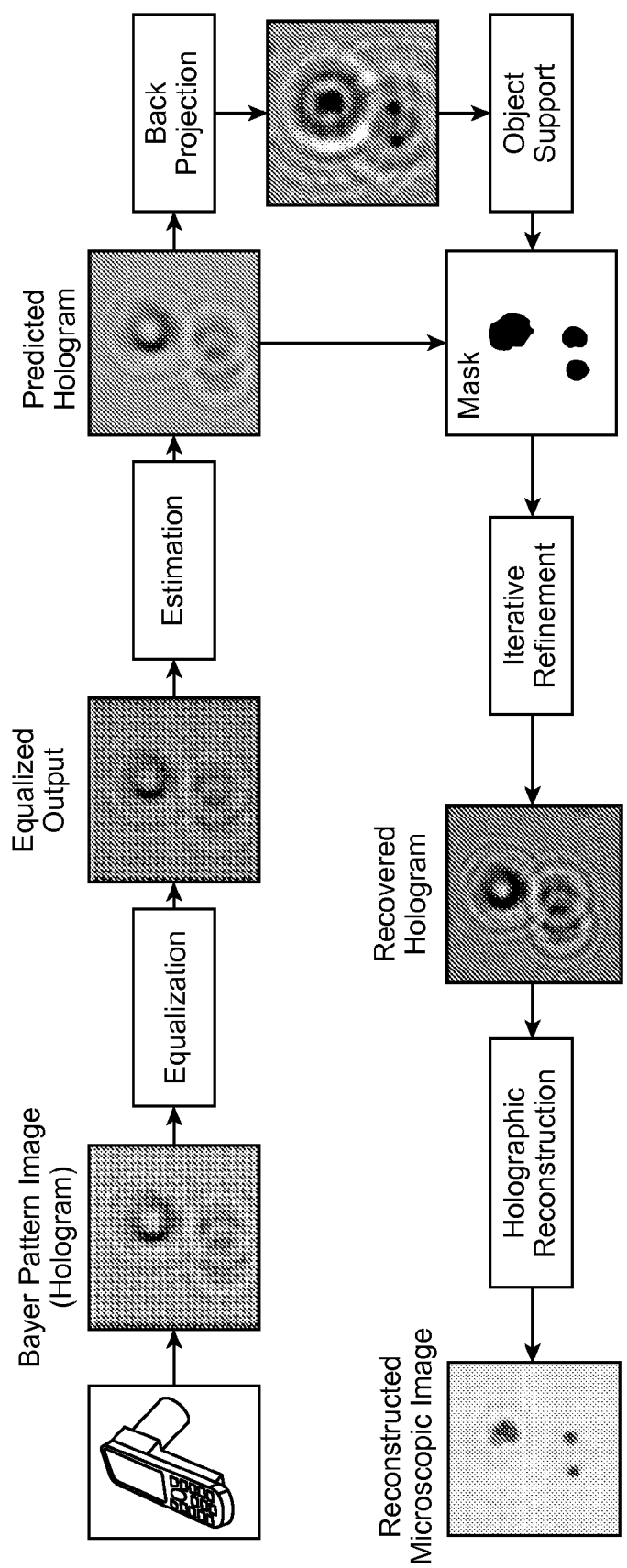
FIG. 4 illustrates a schematic representation of the de-Bayering algorithm developed to create monochrome holographic images from Bayer-patterned output of the system.

FIG. 4 illustrates a schematic representation of the de-Bayering algorithm developed to create monochrome holographic images from Bayer patterned output of our system 10. Red and Green channels of the acquired raw holographic image are equalized using a background image that was recorded with identical illumination conditions as the object. Blue pixels are estimated from their Red and Green neighbors (which include high SNR information) using an edge-aware interpolation approach and are further refined through an iterative recovery process with the help of an automatically generated object support mask. Finally, the recovered hologram is up-sampled and fed into a holographic reconstruction algorithm to create the corresponding microscopic images of the objects.

Figure 5:
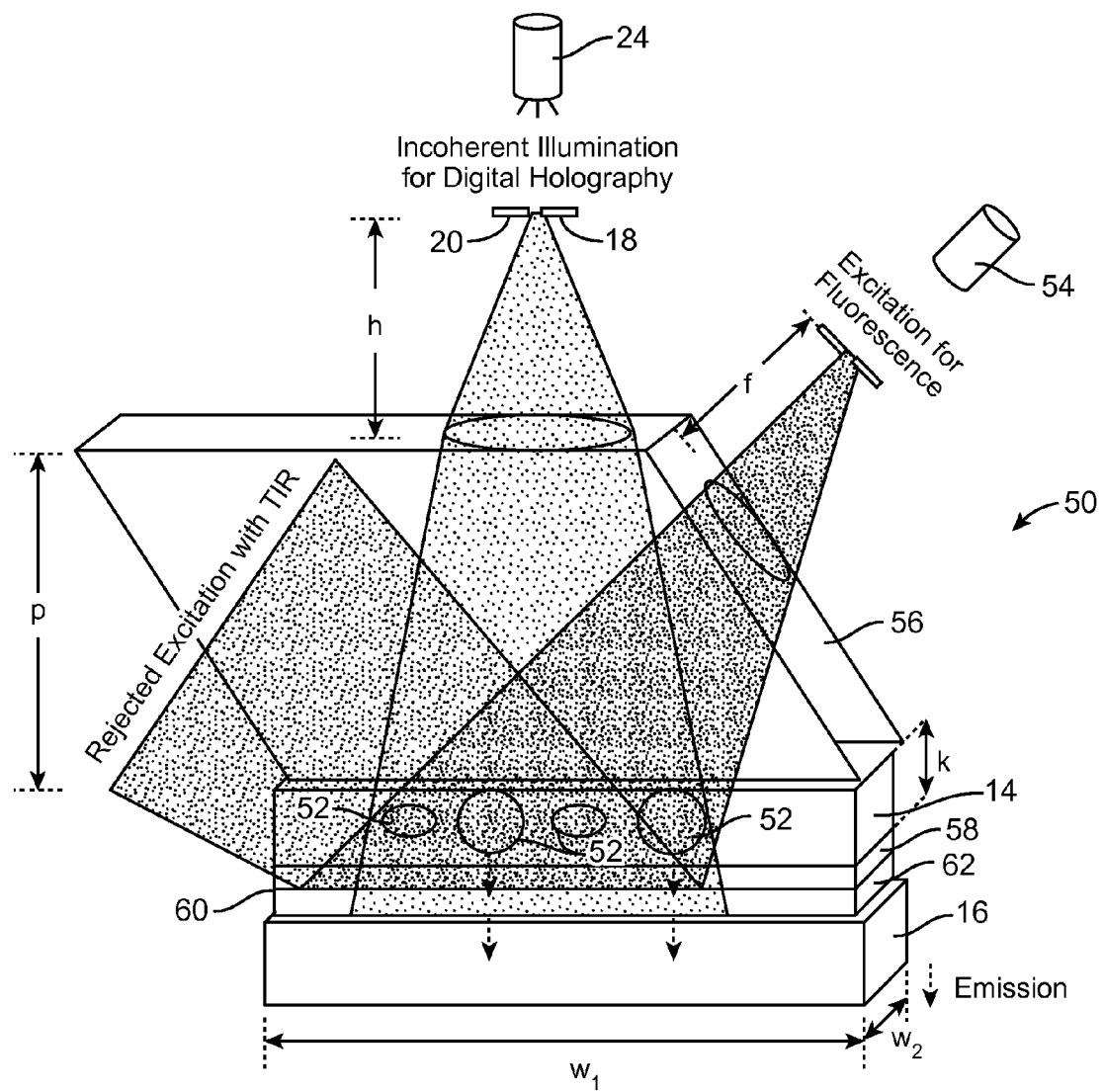
FIG. 5 illustrates another embodiment of incoherent lensfree cell holography and microscopy system that includes fluorescent imaging functionality.

FIG. 5 illustrates a system 50 according to another embodiment of the invention. In this alternative system 50, an on-chip imaging platform includes or merges lensfree holographic imaging (e.g., FIG. 1) with lensfree fluorescent detection over a large field of view. The system includes the illumination source 24 that provides the source of incoherent illumination for digital holography as explained above. Also included is the spatial filter 18 along with the aperture 20. The system 50 further includes a sample holder 14 that contains the sample 12 therein. The sample 12 includes micro-objects such as cells 52 as illustrated in FIG. 5. The sample holder 12 may include a microfluidic-based device that contains channels or the like for carrying or transporting the cells 52.

Still referring to FIG. 5, the system 50 includes a fluorescent excitation source 52 that is configured to emit radiation at one or more wavelengths for fluorescent excitation. The source 52 may include a LED or Xenon lamp tuned by a monochromator. The fluorescent excitation source 52 is preferably oriented at an angle with respect to the sample holder 14. The fluorescent radiation from the fluorescent excitation source 52 is delivered to the sample volume through a prism 56 (e.g. rhomboid prism). Located underneath the sample holder 14 is a layer of glass 58 that is used to reflect the excitation radiation through total internal reflection (TIR) surface 60. The layer of glass 58 may have a thickness on the order of about 100 μm. An imaging sensor array 16 is disposed on the backside of the layer of glass 58 which is used to capture holographic images as well as fluorescent images. Interposed between the TIR glass layer 58 and the imaging sensor array 16 is an adsorption filter 60. The adsorption filter 60 is generally thin having a thickness generally less than 100 μm.

As seen in FIG. 5, the height of the prism 56 was 17 mm. The dimension ($w_1 \times w_2$) of the imaging sensor array 16 is 25×35 mm. The depth of the solution reservoir, k was between 10-100 μm. The distance of the vertical source, h was around 5-10 cm). The distance of the fluorescent excitation source, f was around 1-2 cm. It should be understood that other dimensions beyond those specifically mentioned above are intended to fall within the scope of the invention. Not shown in FIG. 5 but is optional, an index matching-gel can also be used to avoid TIR and undesired scattering at the bottom facet of the prism 56. The thin absorption filter 62 illustrated in FIG. 5 acts as a protective layer in this case, isolating the active region of the imaging sensor array 16 from the micro-channels of the sample holder 14. An exemplary absorption filter 62 may be obtained from Roscolux (e.g., 30 dB for <600 nm; 0.075 mm thick) (Rosco Laboratories, Inc., Stamford, Conn.).

After excitation of the particles/cells, the fluorescent radiation "pump beam" is filtered out through total internal reflection (TIR) at the TIR surface 60. The same top or flat prism 56 interface also permits incoherent lensfree holography to be performed simultaneously for the same field of view. The center of mass of each fluorescent spot in lensfree images overlaps in 2D space with the fluorescent particles' reconstructed holographic images, which enables separation of fluorescent particles from each other and from non-fluorescent ones within the same field of view. Such a dual-imaging capability is quite useful especially to increase the specificity and the functionality of lensfree on-chip imaging. These results would not have been possible with other lensless holographic approaches since with a large sample-sensor distance (e.g., ≥1 mm) each fluorescent spot would then be rather challenging to detect on a chip without the use of any lenses.

The lensfree dual-imaging configuration illustrated in FIG. 5 has several advantages. First, the use of TIR to block the excitation beam is quite efficient in rejection of high pump powers and works independent of the excitation and emission wavelengths. In addition, the detection numerical aperture (NA) of the system 50 is close to 1.0 since the large-area imaging sensor array 16 (e.g., 3.5 cm×3.5 cm) is placed very close to the fluorescent micro-objects, making it highly efficient for photon detection. In other words, only the oblique fluorescent rays that make up the numerical aperture between ~1 and ~1.3 (refractive index of the medium inside the channel) are lost without reaching the detector-array. Meanwhile, unlike a lens-based microscope, this large detection numerical aperture does not directly contribute to spatial resolution in the system 50 due to its lensless operation.

This TIR surface 60 is also quite useful since it avoids the use of thin-film based fluorescent filters, which are wavelength and illumination direction dependent making them inconvenient and costly for lensfree operation. In addition, an inexpensive plastic-based absorption filter 62 may be used to filter out the weakly scattered excitation light that does not obey TIR. The requirements on this filter's performance are greatly reduced due to TIR's efficiency in rejecting the excitation beam, i.e., an inexpensive absorption filter 62 with less than a 30 dB rejection ratio would be sufficient for lensfree fluorescent on-chip imaging.

Figure 6A:
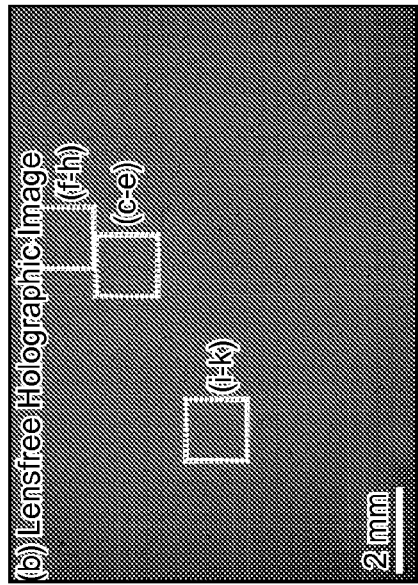

FIGS. 6(a)-6(k) illustrates lensfree holographic and fluorescent imaging of the same field of view that is obtained sequentially for a heterogeneous solution. By controlling the timing of the excitation and holographic imaging beams (e.g., illumination source 24 and fluorescent excitation source 54), one can record both fluorescent and holographic images of the same field-of-view without the use of any lenses, lasers, thin-film filters or other mechanical components. FIG. 6(a) illustrates the lensfree fluorescent image of heterogeneous solution consisting of 10 µm fluorescent (excitation/emission center λ: 580 nm/605 nm), 10 µm NON-fluorescent, 20 µm NON-fluorescent microbeads. As expected only the fluorescent particles show up in this image. Integration time for this image was one second.

Figure 6B:
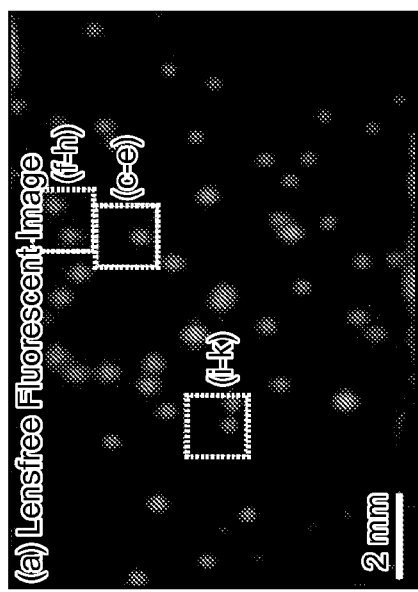
Figure 6C:
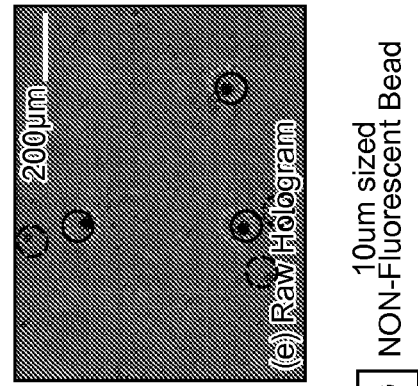
Figure 6D:
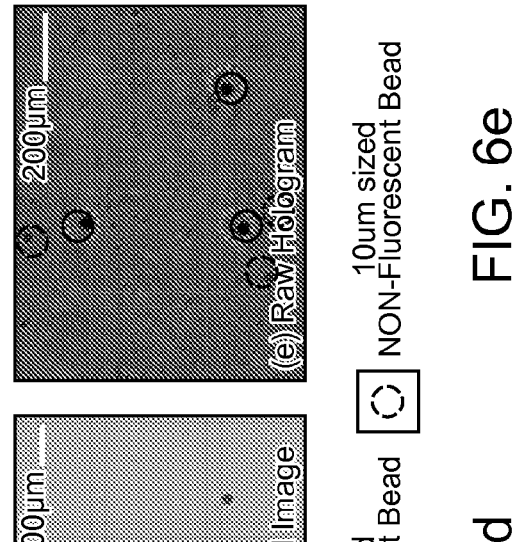
Figure 6E:
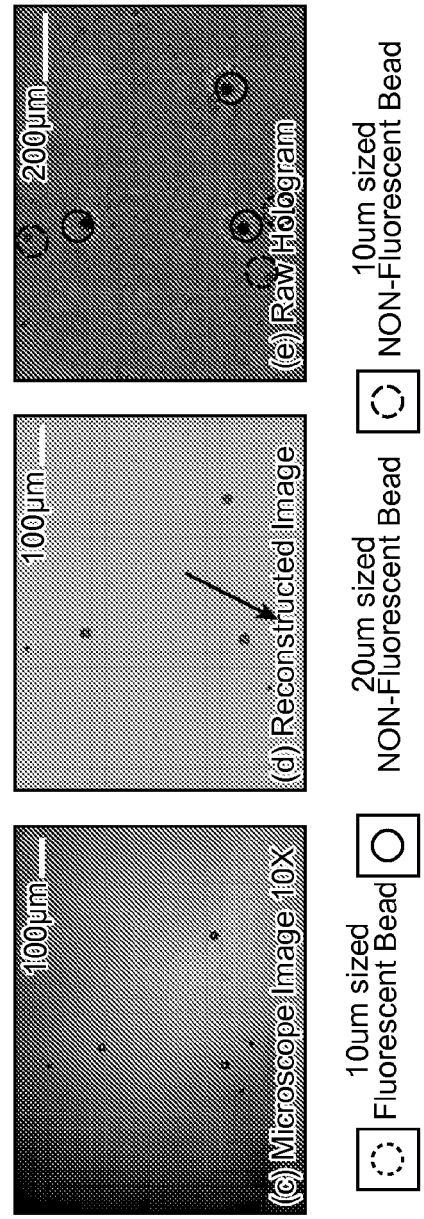

FIG. 6(b) illustrates lensfree holographic image of the same field-of-view is shown, where this time all the particles within the solution cast a shadow on the sensor. FIG. 6(e), (h), and (k) are zoomed regions of interest taken from the raw hologram image shown in FIG. (b). FIGS. (d), (g), and (j) are reconstructed images of the same zoomed regions. As expected all the particles are present in this reconstructed holographic image. FIG. 6(c), (f), and (i) are transmission microscope images of the same field of view for comparison purposes. Based on the lensfree fluorescent image of the same field of view, one can identify fluorescent particles from the non-fluorescent ones within the reconstructed holographic image. Notice that the holographic reconstruction results do not get affected by the granular structure of the absorption filter 62, which enables the use of rather cost-effective components with low cost.

While FIGS. 6(a)-6(k) illustrate imaging of fluorescent beads, the same system 50 may be used to image biological objects such as cells or even whole organisms. The system 50 has been used, for example, for lensfree on-chip fluorescent imaging of transgenic Caenorhabditis elegans (C. elegans) over an ultra-wide field-of-view (FOV) of e.g., >2-8 cm$^2$ with a spatial resolution of ~10 µm. A system 50 like that illustrated in FIG. 5 was used to image C. elegans. After interacting with the entire body of the worm, pump photons are rejected by TIR occurring at the TIR surface 60. To create a sufficient dark-field background, the weakly scattered pump photons that do not obey TIR are also rejected by an additional absorption filter 62, as a result of which only the fluorescent emission from the objects is detected by the imaging sensor array 16.

Note that unlike conventional lens-based fluorescent microscopy, the use of thin-film interference filters 62 in our platform is not trivial since rejection of pump photons in a lensfree imaging configuration would require deposition of much thicker interference films to block a large angular range of pump photons. This not only increases the cost but also requires the use of considerably thick substrates due to higher stress in the thicker film, which significantly weakens the SNR of the fluorescent point-spread function (PSF), also degrading the achievable resolution. Therefore, absorption-based filters were fabricated that have dyes coated on ultra-thin glass substrates (~30 µm).

The fabrication recipe of the thin absorption filters 62 includes dissolving Orasol dyes in a small volume of cyclopentanone and then adding KMPR 1005 Photoresist (~0.4 g ml-1 dye concentration), after which excess dye material was removed using a 0.45 µm diameter mechanical filter. This step is followed by spin coating for 20 seconds at 2000 rpm, baking for 300 seconds at 100° C., flood exposure at 13 mW/cm$^2$ for 35 seconds, and finally baking for another 120 seconds at 100° C. Based on this recipe, different long pass absorption filters were fabricated with cut-off wavelengths of 510 nm, 540 nm and 600 nm by using various types of Orasol dyes, including Yellow 2RLN, Orange G, and Red BL, respectively. The rejection ratio (~30-40 dB) of these fabricated absorption filters is sufficiently large to create the necessary dark-field background (together with TIR), making them rather useful in lensfree fluorescent on-chip imaging applications.

Once fabricated, these absorption filters (total thickness ~40 µm; 10 µm filter+30 µm glass substrate) were placed directly on the top of the active region of the imaging sensor array 16, acting also as a protector layer for the bare sensor surface. An additional disposable ultra-thin glass substrate (~30 μm thick) was also used between the sample and the absorption filter 62.

As for the excitation, an incoherent light source 54 was used, which was coupled from a Xenon lamp spectrally tuned to ~580 nm (with 15 nm bandwidth) through a monochromator (MS260i, Newport). During the experiments, the total power of excitation was kept at ~1.0-1.5 mW for an FOV of >2 cm².

In addition to lensfree fluorescent imaging, the same on-chip platform shown in FIG. 5 also permits lensfree holographic imaging of the same samples through the top facet of the same prism 56 that is used in fluorescent excitation. This vertical illumination is achieved by an incoherent source 24 (i.e., an LED, 632 nm peak, and ~20 nm bandwidth) that is spatially filtered with an aperture 20 (~0.05-0.1 mm) to achieve holographic transmission imaging within the same on-chip platform.

Transgenic *C. elegans* used in the investigation is widely studied to better understand the connections between muscle cells and related motor neurons. For this end, UNC 122 gene is co-injected into the worms with a phenotypic marker (mCherry; emission wavelength: 610 nm). For preparation of these transgenic *C. elegans* samples toward on-chip imaging, a small chunk of nematode growth medium (NGM) was extracted from the culturing plate with a sterilized tool. This specimen was dissolved in a paralyzing medium (~200 μL) that was prepared with 10 mM of Levamisole. To detach the worms from the gel medium, the aliquot is gently vortexed and centrifuged. By using a pipette, transgenic worms are then transferred to sample holders 14 for lensfree on-chip imaging.

An immobilization reagent, i.e. Levamisole, was used to avoid hazy images, which also enabled the capture comparison images of the same samples using a conventional fluorescent microscope. Note also that to avoid physical damage to adult worms, mechanical spacers such as non-fluorescent particles (~50-100 μm diameter) were also used in the imaging experiments.

Figure 7:
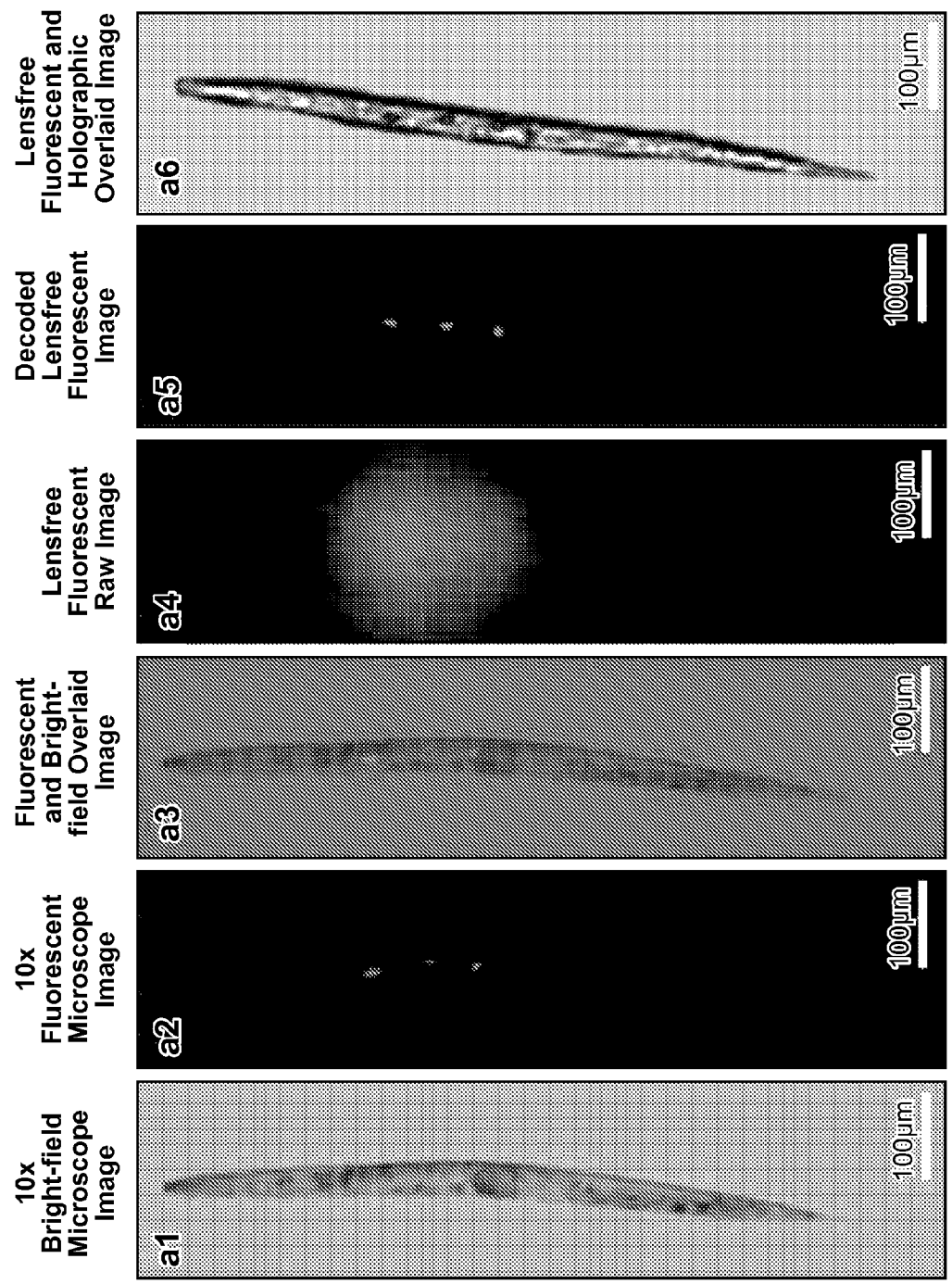
FIG. 7 illustrates lensfree on-chip fluorescent images of transgenic C. elegans.
Figure 7:
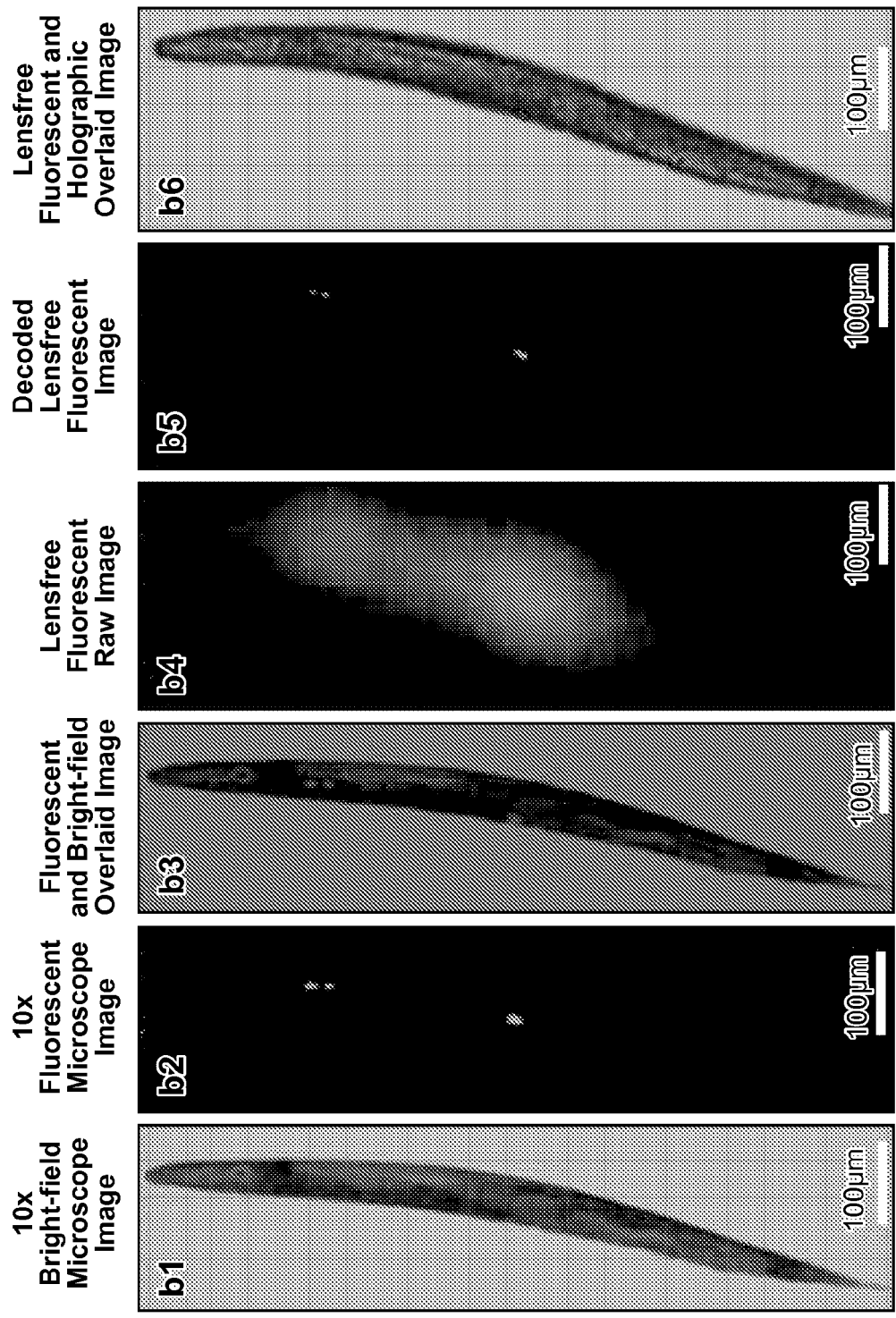
Figure 8:
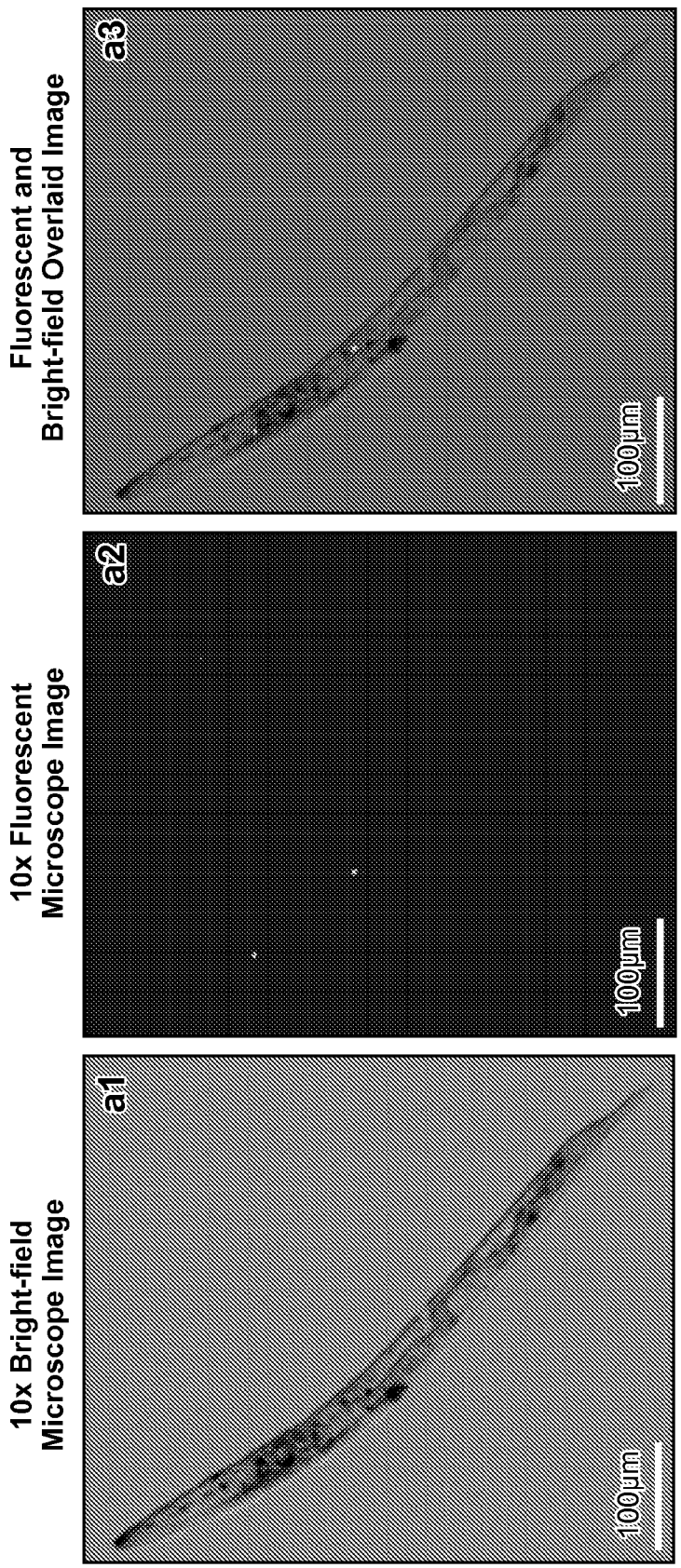
FIG. 8 illustrates lensfree on-chip fluorescent images of transgenic C. elegans using a different imaging sensor array.
Figure 8:
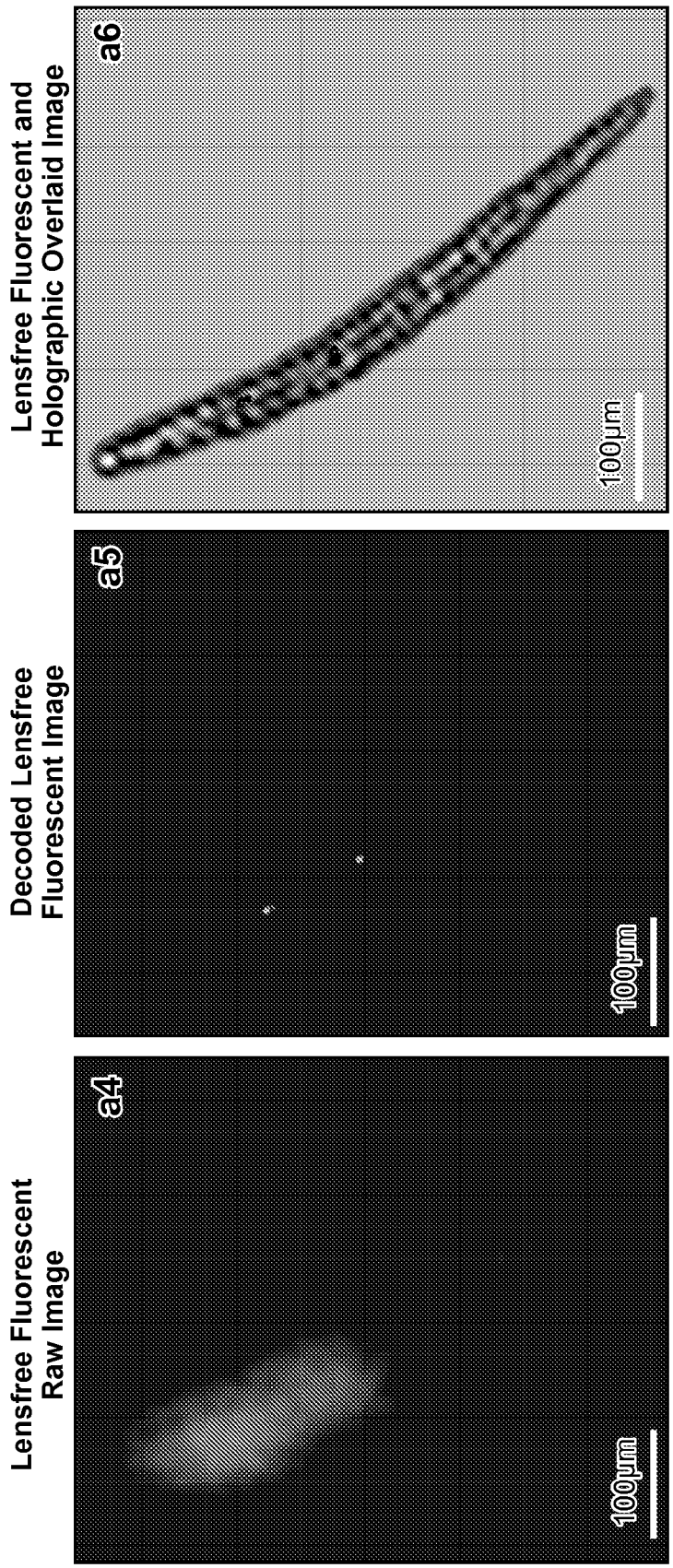

The results of these imaging experiments are summarized in FIGS. 7 and 8 which also provide conventional fluorescent microscope images of the same samples for comparison purposes. Raw lensfree fluorescent signatures of the worms are highly blurred due to the broad PSFs. However, using the measured PSF of each platform, these lensfree signatures can be compressively decoded to digitally yield much higher resolution images of the fluorescent regions located within the *C. elegans* body, which very well agree with the images obtained using a regular lens-based fluorescent microscope.

FIG. 7 illustrates lensfree on-chip fluorescent images of transgenic *C. elegans* is shown for three individual animals using KAF-8300 imaging sensor array 16 (KODAK KAF-8300-5.4 μm pixel size, ~2.4 cm2 active imaging area). Images (a4), (b4) and (c4) illustrate the lensfree fluorescent raw images that all look blurry at the detector plane. Compressive decoding, discussed in more detail below, of these blurry patterns enabled digital reconstruction of much higher resolution fluorescent images of these *C. elegans* samples as shown in (a5), (b5) and (c5), respectively. Further, 10× objective-lens fluorescent microscope images of the same worms shown in (a2), (b2) and (c2) agree well with the decoded lensfree fluorescent images. In addition to fluorescent imaging, the same lensfree platform also permits holographic transmission imaging of the same samples such that hybrid images can be created by superimposing the decoded lensfree fluorescent images and the reconstructed holographic images as shown in (a6), (b6) and (c6).

Microscope comparisons of the same samples are also provided in (a3), (b3) and (c3), respectively. Slight rotations of the worms are observed between the lensfree decoded images and their microscope comparison images since they are acquired at different experiments.

FIG. 8 illustrates lensfree on-chip fluorescent images of transgenic *C. elegans* is shown using KAF-11002 imaging sensor array 16 (KODAK KAF-11002—9 μm pixel size, 11 MPixel). Similar to FIG. 7, the decoded lensfree fluorescent image of the transgenic *C. elegans* sample provides a good match to a conventional fluorescent microscope image of the same worm (acquired with a 10× objective-lens, NA=0.25). Slight rotation of the worm is observed between the lensfree decoded image and its microscope comparison image since the two are acquired at different experiments.

Compressive decoding enables accurate reconstruction of the fluorescent distribution at the object plane based on the measured PSF of the lensfree imaging platform, achieving a spatial resolution of e.g., ~10 μm over >2-8 cm² FOV. This numerical recipe relies on compressive sampling theory which presents a new method to reconstruct a sparse signal from its under-sampled representation. Wide-field fluorescent imaging of *C. elegans* samples on a chip by definition brings sparsity to the imaging problem since most of the FOV is already dark (i.e., non-fluorescent). Based on this connection to compressive sampling theory, lensfree raw fluorescent images can be rapidly decoded (using the measured fluorescent PSF) to significantly improve the resolving power of the platform.

This compressive decoding process can be formalized as an $l_1$-regularized least square problem, such that:

$$\hat{i} = \text{argmin} \| F_{det} - P_{conv} \cdot \vec{i} \|_2 + \alpha \cdot \| \vec{i} \|_1 \qquad \text{Eq. (1)}$$

where $F_{det}$ is the detected raw fluorescent image at the sensor-array; $P_{conv}$ represents the 2D convolution matrix based on the fluorescent PSF of the system; $\vec{i}$ is the fluorescent source distribution that creates the lensfree image at the plane of the imaging sensor array 16; α is a non-negative regularization parameter; and $\|\vec{x}\|_p$ represents the $l_p$ norm of vector $\vec{x}$. The optimization algorithm used in this work is based on truncated Newton interior-point method which rapidly converges to a sparse fluorescent solution ($\hat{i}$) based on Eq. (1).

These experimental results successfully demonstrate the efficacy of the compressive decoding approach to image transgenic *C. elegans* samples using lensfree fluorescent on-chip imaging over an ultra-wide FOV that covers the entire active area of the CCD chip (e.g., >2-8 cm²). As explained above, in addition to fluorescent imaging, the system 50 also permits holographic transmission imaging of the worms using the top interface of the prism 56 that is used in fluorescent excitation. In this lensfree holographic imaging approach, a spatially incoherent quasi-monochromatic source 24 such as a light-emitting-diode (LED) illuminates the samples of interest after being spatially filtered by a large aperture 20 (e.g., 0.05-0.1 mm diameter). This incoherent light source picks up partial spatial coherence that is sufficiently large to record lensfree in-line holograms of the worms on the imaging sensor array 16. These acquired in-line holograms can then be rapidly processed using iterative recovery algorithms to create lensfree transmission images of the *C. elegans* samples over the entire active area of the imaging sensor array 16, matching the imaging FOV of the fluorescent channel. FIGS. 7 and 8 illustrate such reconstructed lensfree holographic images of the samples, where the lensfree fluorescent images of the same worms were also digitally super-imposed, creating a hybrid image of the *C. elegans* (i.e., both fluorescent and transmission). It is evident from these lensfree images that the spatial resolution of the platform is modest compared to a regular lens-based microscope. On the other hand, the main advantages of our platform are its ultra-wide FOV and compact design which provides an important match for ultra-high throughput screening of *C. elegans* samples within automated micro-fluidic systems.

Figure 9:
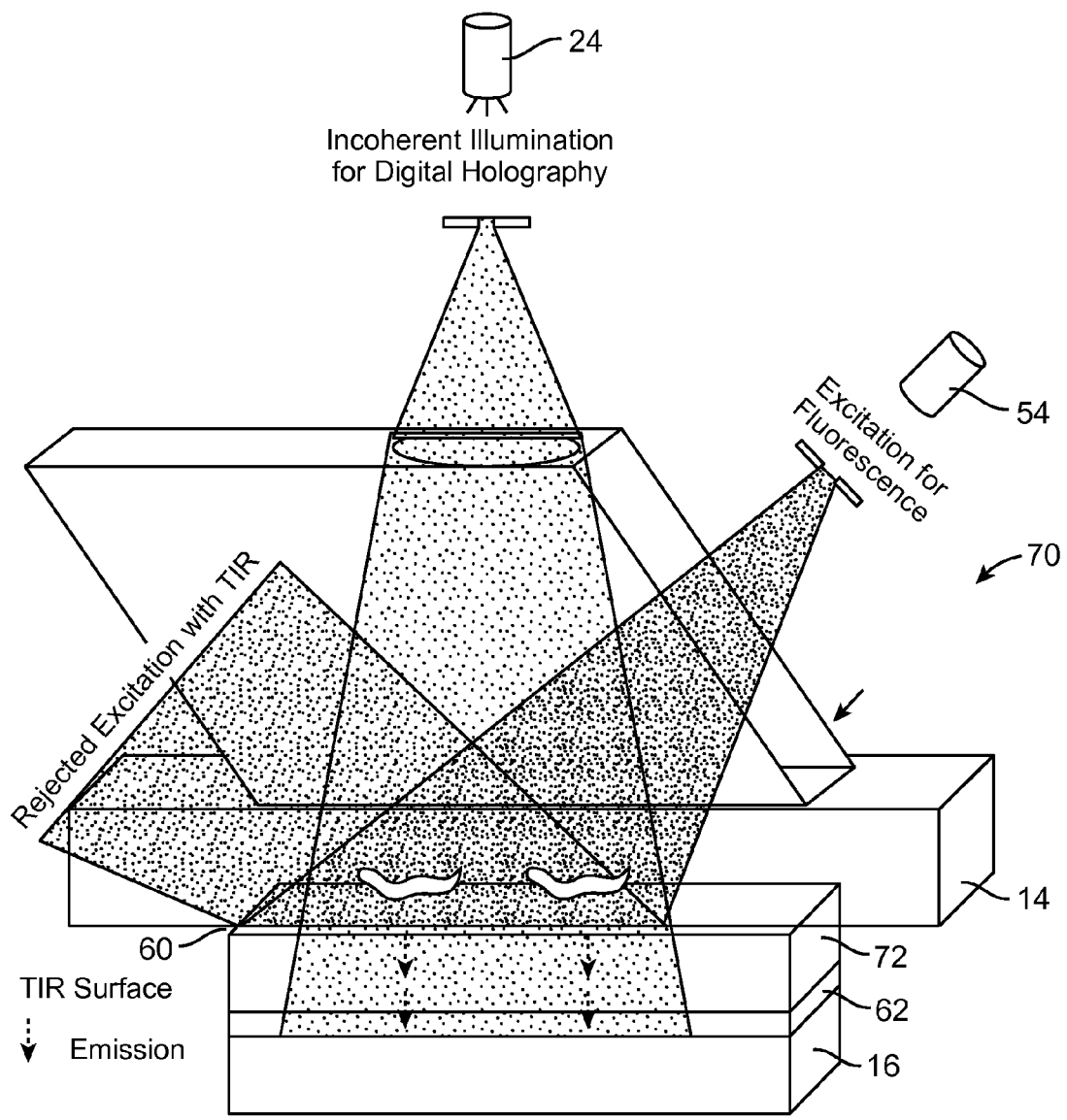
FIG. 9 illustrates another embodiment of incoherent lensfree cell holography and microscopy system that includes fluorescent imaging functionality.

FIG. 9 illustrates an alternative lensfree imaging system 70 that can also perform fluorescent imaging of *C. elegans* samples. In this modified configuration, a fiber optic-faceplate 72 is inserted underneath the sample holder 14 to control and tailor the fluorescent PSF of the imaging platform. Compressive decoding of transgenic *C. elegans* samples using these altered fluorescent PSFs yields similar imaging results as in FIGS. 7 and 8. This modified system 70 can conveniently tailor the fluorescent PSF of the imaging platform to enhance the detection SNR, especially at larger gaps between the object and sensor planes. This could be an important advantage if physical separation between the sample 12 and the imaging sensor array 16 is required.

Figure 10B:
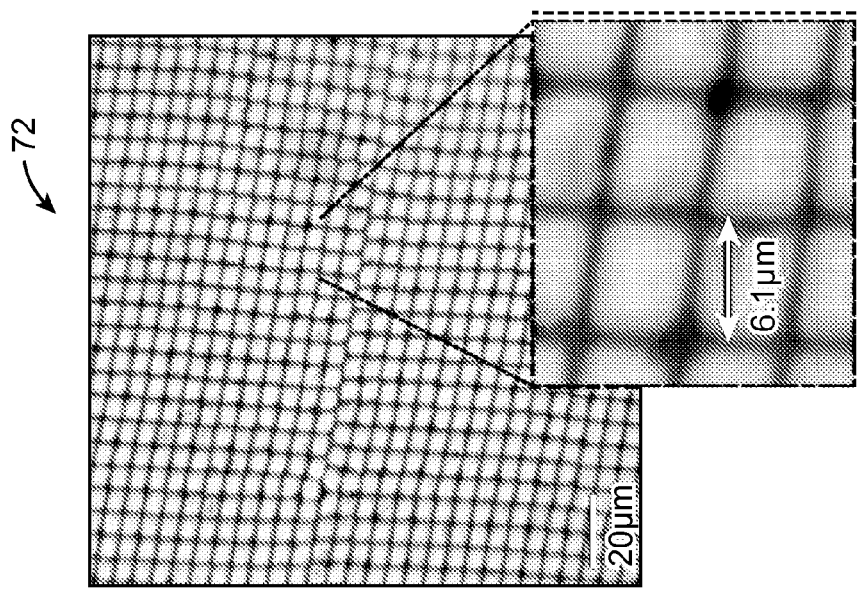
FIG. 10B illustrates a microscope image of the optic-faceplate.
Figure 10A:
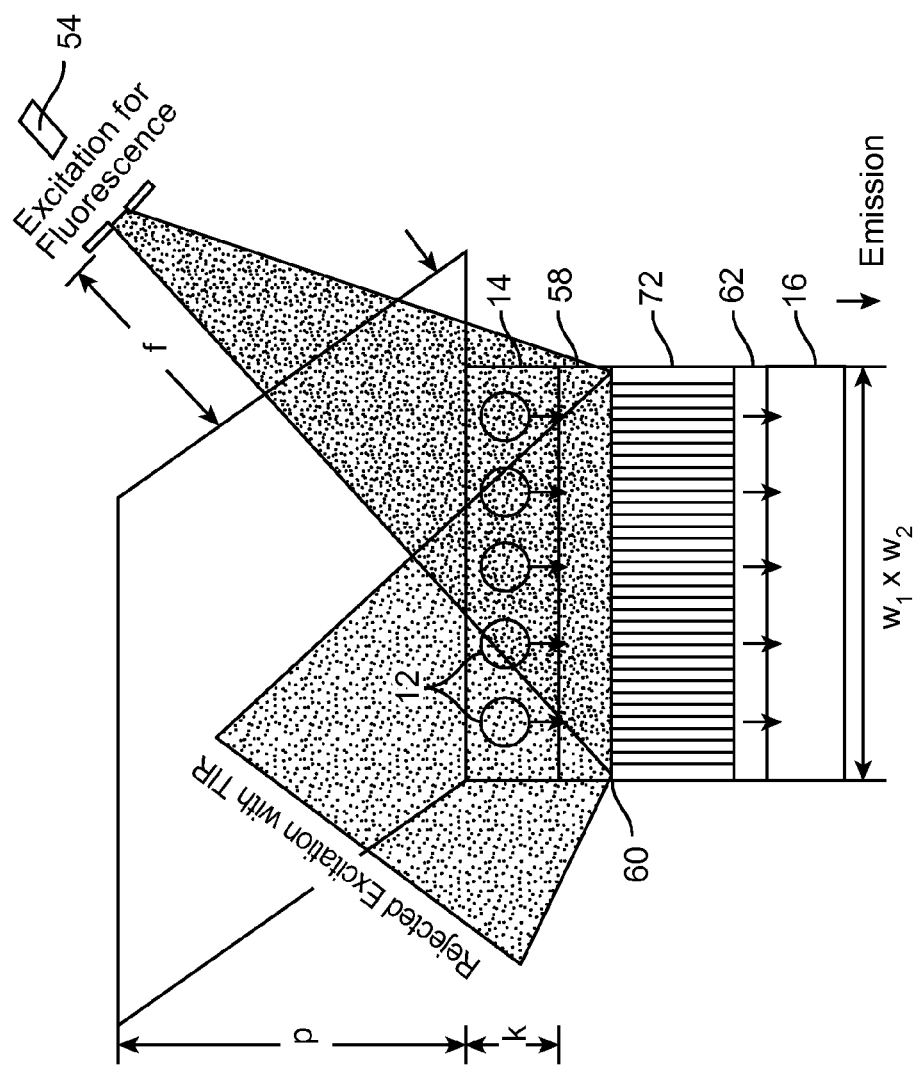
FIG. 10A illustrates an embodiment of incoherent lensfree cell holography and microscopy system that includes fluorescent imaging functionality along with the use of an optic-faceplate.

The use of a fiber optic-faceplate 72 may can be utilized to provide better detection SNR and higher spatial resolution to be achieved. The fiber optic-faceplate 72 delivers the emitted fluorescent light to the imaging sensor array 16. The fiber optic-faceplate generally consists of an array of fibers having a thickness of about 1 cm with each fiber having a numerical aperture of about 0.3. FIG. 10A illustrates a schematic representation of the lensfree on-chip fluorescent imaging system 70. This imaging system 70 has unit magnification such that the imaging field-of-view equals to the entire active area of the sensor array (i.e., >8 cm$^2$). The TIR condition occurs at the glass-air interface at the bottom facet of the cover glass (TIR surface 60). To avoid detection of scattered pump photons a plastic absorption filter is used after the faceplate. Typical dimensions: $w_1 \times w_2 = 25$ mm$\times$35 mm; p=1.7 cm; k~10-100 µm; f=1-2 cm. FIG. 10B illustrates a microscope image of the optic-faceplate 72.

A compressive sampling-based algorithm can be used to rapidly reconstruct the sparse distribution of fluorescent sources to achieve approximately 10 µm spatial resolution over the entire active region of the sensor-array, i.e., over an imaging FOV of >8 cm$^2$. Such a system 10 could especially be significant for high-throughput imaging cytometry, rare cell analysis, as well as for micro-array research. Additional details regarding the compressive sampling-based algorithm can be obtained from Coskun et al., Lensless wide-field fluorescent imaging on a chip using compressive decoding of sparse objects, Optics Express, Vol. 18, Issue 10, pp. 10510-10523 (2010), which is incorporated by reference as if set forth fully herein.

When compared to earlier lensfree fluorescent imaging work, the fiber optic-faceplate 72 results in an improvement of ~5 fold in spatial resolution without a trade-off in FOV, which we attribute to the use of the fiber-optic faceplate and the compressive sampling based numerical processing. Furthermore, with this alternative system 70, lensfree fluorescent imaging of vertically stacked microchannels is used, all in parallel, further increasing the throughput. This particular system 70 is well suited for applications in which the target cells of interest are rare such as circulating cancer cells in whole blood.

Figure 11:
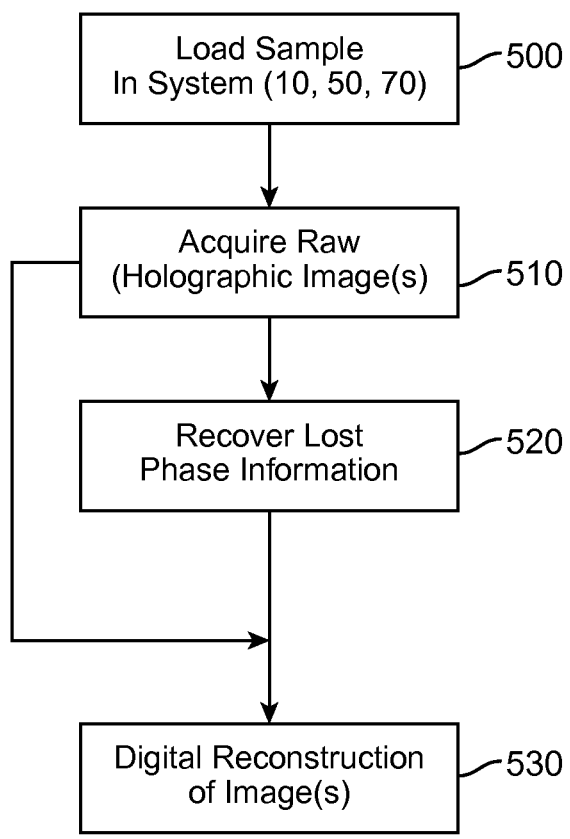
FIG. 11 illustrates a top-level flowchart of how the systems digitally reconstruct an image of the object of interest.

As explained herein, the systems 10, 50, 70 utilize an imaging sensor array 16 to obtain raw hologram amplitude images of the object of interest. The lost hologram phase is then recovered. The recovered phase information together with the measured amplitude information is used to digitally reconstruct an image of the object of objects of interest. FIG. 11 illustrates a top-level flowchart of how the systems 10, 50, and 70 digitally reconstruct an image of the object of interest. As seen in operation 500 of FIG. 11, a sample 12 is loaded into the system 10, 50, 70. Raw holographic images are then obtained in operation 510. The "lost" phase information is then recovered in operation 520. Based on the recovered phase information and the raw holographic images, one or more images of the sample are then digitally reconstructed as outlined in operation 530.

For digital reconstruction of the object images from their holograms there are two approaches that were taken: (1) Back-propagate the Fourier components of the intensity of each object hologram; and (2) Recover the 2D phase of the amplitude of each hologram. These two techniques independently enabled twin-image free reconstruction of the microobjects from their raw holograms. These digital reconstruction approaches can actually be considered to be part of a broader umbrella of Interferometric and Non-interferometric Phase-Retrieval Techniques. In both of these approaches, the transfer function of the Rayleigh-Sommerfeld integral without any approximations has been used for back-propagating the fields.

The first approach mentioned above works with the intensity of the detected holograms, and is susceptible to the well-known twin image problem. To eliminate the twin image artifact in this first approach a numerical algorithm was implemented that can iteratively clean the reconstructed images from the twin image. In the second reconstruction method, the amplitudes of the lensfree holograms (rather than their intensities) are used to recover the 2D phase information of the complex diffraction field that was lost during the detection process. This phase recovery step is further useful as it also creates another unique 2D texture for each cell type such that these recovered 2D phase holograms can also be utilized for characterization of a heterogeneous solution. Once the entire complex diffraction field is recovered, the microscopic image can be calculated without any twin image artifact through back-propagation of the complex field.

For incoherent cell holography both of these approaches yield very similar recovery results. However, for larger scale microorganisms the 2D phase recovery approach discussed above has certain advantages. For a large organism, the scattered light fields cannot always effectively interfere with the background light, such that the holographic diffraction terms start to lose their relative strengths. However, the phase recovery approach treats the detected quantity as the amplitude of a complex diffraction field, and tries to iteratively recover its phase for digital reconstruction. Therefore the phase recovery based reconstruction approach is especially useful for lensfree imaging of highly scattering cells or larger scale organisms where the cross-interference terms start to dominate over holographic diffraction. As a trade-off, the space-bandwidth product that is required at the detector end is increased by two fold for the phase recovery technique when compared to the first approach, since the latter one does not only deal with the holographic diffraction term, but also deals with self-interference terms.

The microscopic reconstruction can utilize successive fast Fourier transform (FFT) operations, where after the initial FFT of each iteration, transfer function of Rayleigh-Sommerfeld integral without any approximations has been applied to the Fourier components of the cell hologram. Because FFT is used, the presented recoveries are also quite fast in terms of digital computation time, with a convergence time of less than a few of seconds using e.g., a 1.6 GHz Pentium Processor.

Despite significant practical advantages of the proposed incoherent cell holography system 10, 50, 70, incoherent illumination will not increase the burden on the numerical reconstruction process. For incoherent lensfree cell holography with M>>1, each individual cell can still be treated to be illuminated with a coherent light. Furthermore, due to their microscopic cross-sections, the incident wave on each micro-object (e.g., cell) can be assumed to be a plane wave. Consequently, the reconstruction of each recorded cell hologram can be performed assuming plane-wave illumination.

In order to diffract the wavefronts, the angular spectrum approach is used to numerically solve the Rayleigh-Sommerfeld integral. This computation involves multiplying the Fourier transform of the field with the transfer function of propagation through linear, isotropic media, as shown below:

$$H_z(f_x, f_y) = \begin{cases} \exp\left(j2\pi z \frac{n}{\lambda}\right) \sqrt{\frac{1-(\lambda f_x/n)^2 - }{f(\lambda f_y/n)^2,}} & \sqrt{f_x^2 + f_y^2} < \frac{n}{\lambda} \\ 0, & \text{otherwise} \end{cases} \quad \text{Eq. (2)}$$

where $f_x$ and $f_y$ are the spatial frequencies and is the refractive index of the medium.

Two different iterative approaches, as explained above, are taken in order to reconstruct the microscopic images of cells, free from any twin-image artifact. Both methods work with a single recorded hologram and rely on the constraint that each cell has a finite support. In both methods, the raw holograms are upsampled typically by a factor of four to six, using cubic spline interpolation before the iterative reconstruction procedure. Although upsampling does not immediately increase the information content of the holograms, it still offers significant improvements for achieving a more accurate phase recovery and higher resolution in the reconstructed image. First, it allows defining a more accurate object support by smoothing the edges of the objects in the initial back-projection of the hologram. Using an object support that is closer to the actual cell in terms of size and shape reduces the error of the iterative algorithms, as well as ensuring faster convergence. Second, upsampling introduces higher spatial frequencies initially carrying zero energy, in the hologram. Through the iterative reconstruction steps detailed below, these higher spatial frequencies gradually attain non-zero energy, which allows sub-pixel resolution in the final reconstruction.

Method 1:

The first method falls under the broad category of Interferometric Phase-Retrieval Techniques and is applicable to cases where the recorded intensity is dominated by the holographic diffraction terms. The first step is the digital reconstruction of the hologram, which is achieved by propagating the hologram intensity by a distance of $z_2$ away from the hologram plane yielding the initial wavefront $U_{rec}$. As a result of this computation, the virtual image of the object is recovered together with its spatially overlapping defocused twin-image. It is important to note that the recorded intensity can also be propagated by a distance of $-z_2$. In this case, the real image of the object can be recovered, while the defocused virtual image leads to the twin-image formation.

Due to the small cell-sensor distance in the incoherent holographic microscopy scheme presented here, the twin-image may carry high intensities, especially for relatively large objects like white blood cells. In such cases, the fine details inside the micro-objects may get suppressed. Similarly, the twin-images of different cells which are close to each other get superposed, leading to an increase in background noise. This issue is especially pronounced for microscopy of dense cell solutions, where the overlapping twin images of many cells lowers the counting accuracy due to reduced SNR.

In order to eliminate the twin-image artifact, an iterative approach using finite support constraints is utilized. Essentially, this technique relies on the fact that duplicate information for the phase and amplitude of the object exists in two different reconstruction planes at distances $+z_2$ and $-z_2$ from the hologram plane, where the virtual and real images of the object are recovered, respectively. Therefore, a twin-image-free reconstruction in one of the image planes can be obtained, while filtering out the duplicate image in the other plane. Without loss of generality, the real image was filtered out to obtain a twin-image-free reconstruction in the virtual image plane at $-z_2$. Due to the finite size of the micro-objects, the real image of the object only occupies the region inside its support, while the defocused twin-image image spreads out to a wider region around the object, also overlapping with the real image inside the support. Hence, deleting the information only inside the support ensures that the real image is completely removed from the reconstructed wavefront. Nevertheless, the virtual image information inside the support is also lost, and the iterative technique tries to recover the missing information of the virtual image by going back and forth between the virtual and real image planes, recovering more of the lost information at each iteration. The success of this algorithm is highly dependent on the Fresnel number of the recording geometry, which is given by $$N_f = \frac{n(\text{object size})^2}{\lambda z} \quad \text{Eq. (3)}$$

It is reported that the technique proves successful for Fresnel numbers as high as 10. For RBCs of approximately 7 μm diameter, the typical recording geometries presented here involve Fresnel numbers of <0.2; hence, the twin-image elimination method yields highly satisfactory results.

The steps of twin-image elimination are detailed below.

a) Initially the real image, which is the back-projected hologram at a distance of $+z_2$, is used for determining the object support. Object support can be defined by either thresholding the intensity of the reconstructed image, or searching for its local minima.

b) The region inside the support is deleted and a constant value is assigned to this region as an initial guess for the deleted part of the virtual image inside the support as shown below:

$$U_{z_2}^{(i)}(x, y) = \begin{cases} U_{rec}, & x, y \notin S \\ \bar{U}_{rec}, & x, y \in S \end{cases} \quad \text{Eq. (4)}$$

Where $U_z^{(i)}(x,y)$ denotes the field at the real image plane after the $i^{th}$ iteration. S represents the area defined by the object support, and $\bar{U}_{rec}$ is the mean value of $U_{rec}$ within the support.

c) Then, the field at the real image plane is back propagated by $-2z_2$ to the virtual image plane. Ideally, the reconstruction at this plane should be free from any twin-image distortions. Therefore, the region outside the support can be set to a d.c. background value to eliminate any remaining out-of-focus real image in the virtual image plane. However, this constraint is applied smoothly as determined by the relaxation parameter β below, rather than sharply setting the image to d.c. level outside the support:

$$U_{-z_2}^{(i)}(x, y) = \begin{cases} D - \dfrac{D - U_{-z_2}^{(i)}}{\beta}, & x, y \notin S \\ U_{-z_2}^{(i)}, & x, y \in S \end{cases} \quad \text{Eq. (5)}$$

where D is the background in the reconstructed field, which can either be obtained from a measured background image in the absence of the object, or can simply be chosen as the mean value of the field outside the object supports at the virtual image plane. β is a real valued parameter greater than unity, and is typically chosen around 2-3. Increasing β leads to faster convergence, but compromises the immunity of the iterative estimation accuracy to background noise.

d) The field at the virtual image plane is forward propagated to the real-image plane, where the region inside the support now has a better estimate of the missing part of the virtual image. The region outside the support can be replaced by $U_{z_2}^{(r)}(x,y)$, the original reconstructed field at the real image plane, as shown below:

$$U_{z_2}^{(i+1)}(x, y) = \begin{cases} U_{z_2}^{(1)}, & x, y \notin S \\ U_{z_2}^{(i+1)}, & x, y \in S \end{cases} \quad \text{Eq. (6)}$$

Steps c to d can be repeated iteratively until the final image converges. In most cases in this article, convergence is achieved after 10-15 iterations, which takes much less than a minute on a computer with a modest hardware configuration.

Method 2:

The second method utilized for eliminating the twin-image is classified under Non-Interferometric Phase-Retrieval Techniques, where the recorded image is not necessarily treated as a hologram, but as the intensity of any diffraction field. Together with the constraint that the objects have finite support, this technique is capable of iteratively recovering the phase of the diffracted field incident on the detector from a single intensity image. As a result, the complex field (amplitude and phase) of the cell holograms, rather than the intensity, can be back-propagated, thereby allowing reconstruction of the objects free from any twin-image contamination. This method can be decomposed into the following steps:

a) The square-root of the recorded hologram intensity is propagated by a distance of $-z_2$ to the cell plane, assuming a field phase of zero as an initial guess. The aim of the algorithm is to iteratively determine the actual phase of the complex field at the detector plane, and eventually at the object plane. In the first iteration, the object support is defined either by thresholding the intensity of the field at the object plane, or by locating its regional maxima and/or minima.

b) The field inside the object supports is preserved, while the complex field values outside the supports is replaced by a background value $D_{-z_2}(x,y)$ as shown below:

$$U_{-z_2}^{i+1}(x, y) = \begin{cases} m \cdot D_{-z_2}(x, y), & x, y \notin S \\ U_{-z_2}^i(x, y), & x, y \in S \end{cases} \quad \text{Eq. (7)}$$

where $D_{-z_2}(x,y)$ is obtained by propagating the square root of the background intensity of the image obtained by the same setup in the absence of the cells; and $m=\text{mean}(U_{-z_2}{}^t(x,y)/\text{mean}(D_{-z_2}(x,y))$.

c) The modified field at the object plane is propagated back to the detector plane, where the field now has a non-zero phase value. The amplitude of this field is replaced with the square root of the original recorded hologram intensity as no modification for the amplitude should be allowed while converging for its phase. Consequently, $U_O^{(t)}(x,y)$, the complex diffraction field at the detector plane after the $i^{th}$ iteration can be written as follows:

$$U_O^{(t)}(x,y)=|U_O^{(O)}(x,y)|\cdot\exp(\phi_0^{(t)}(x,y)) \quad \text{Eq. (8)}$$

where the superscripts denote the iteration step, and $\phi_0^{(t)}(x,y)$ denotes the phase of the field after the $i^{th}$ iteration.

Steps a to c can be iterated until the phase recovery converges. Typically, the results presented in this paper are obtained with less than 15 iterations, which is quite similar to the first Method.

Comparison of Method 1 and Method 2:

For small or weakly scattering objects such as whole blood cells or micro-beads, both methods yield satisfactory results of comparable image quality. For such objects, the typical Fresnel number of the recording geometry is <1 and the focused real image occupies a small fraction of the area over which the twin-image is spread out. Therefore, deleting the object image in the real image plane leads to minimal information loss for the virtual image, which is to be recovered without twin-image artifacts. However, for larger objects of interest the Fresnel number of the system increases, and deleting the real image may causes excessive information loss in the virtual image, which may be harder to recover iteratively. Furthermore, for strongly scattering objects, the self and cross-interference terms may start dominating such that the holographic content of the recorded intensity gets distorted. Therefore for strongly scattering and/or extended objects, the second method discussed above becomes more preferable over the first method, which requires the holographic terms to be dominant in a setup with Fresnel numbers <10. On the other hand, an advantage of the first method is that it does not necessarily require a separate background image taken prior to inserting the sample into the setup. Although a mean value of the field at the object plane can also be used, in the absence of a background image for Method 2 (step b), it was observed that the final image quality becomes better with an experimentally obtained background.

Figure 12:
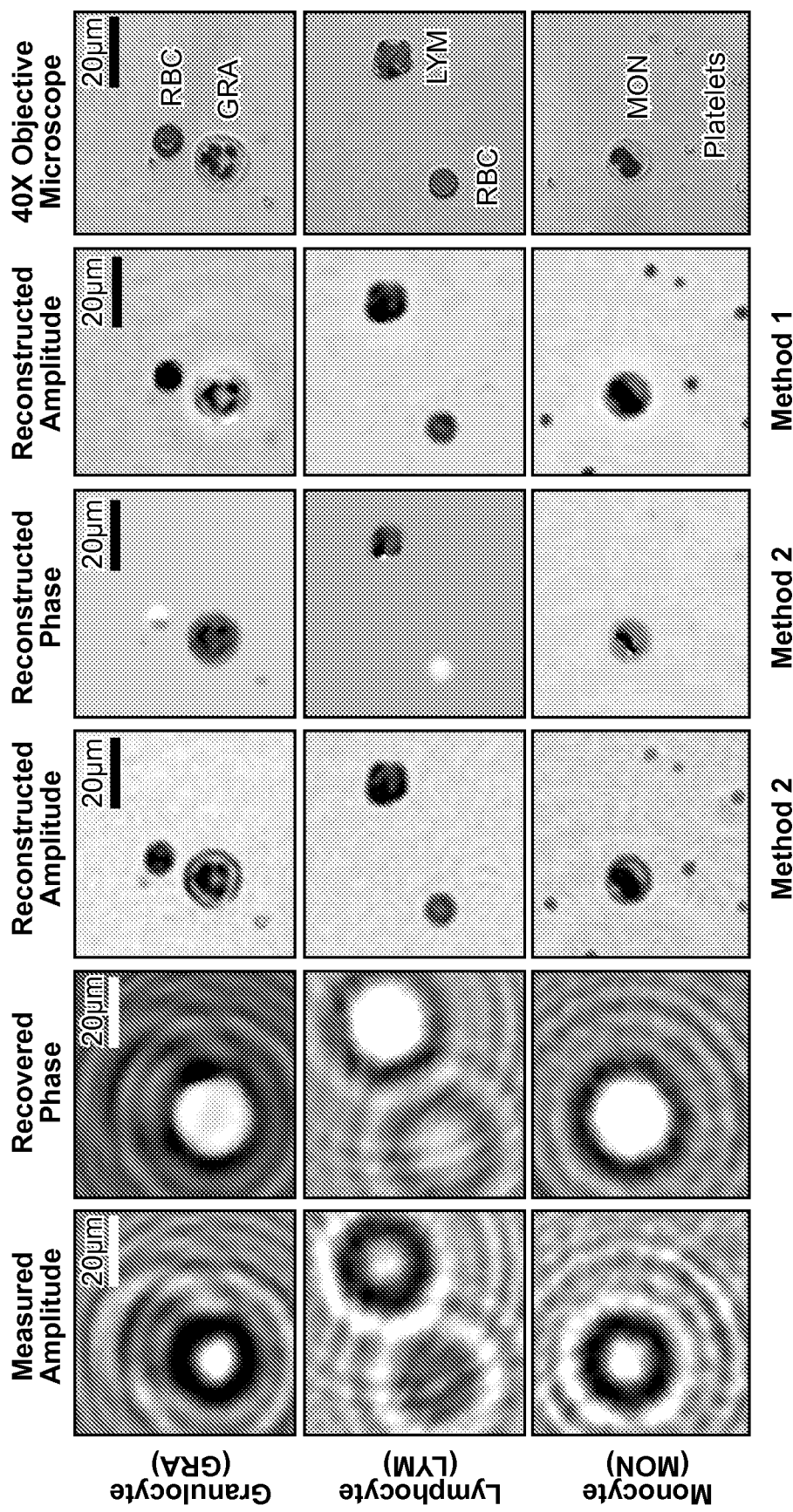
FIG. 12 illustrates incoherent lensfree imaging results of a blood smear sample, illustrating the holographic signatures of three major types of white blood cells (i.e., granulocytes, lymphocytes and monocytes).

FIG. 12 illustrates incoherent lensfree imaging results of a blood smear sample, illustrating the holographic signatures of three major types of white blood cells (i.e., granulocytes, lymphocytes and monocytes). The same field of view in each case is also imaged using a 40× objective lens for comparison purposes (scale bar, 20 μm). Measured hologram amplitudes, recovered hologram phases, reconstructed amplitude and phase images of a granulocyte (GRA), a lymphocyte (LYM) and a monocyte (MON) are illustrated. FIG. 12 also illustrates a comparison between the recover results of Method 1 (iterative twin-image elimination) and Method 2 (iterative phase recovery). RBC refers to red blood cell in the 40× objective lens image. The textural signature of each cell hologram, before a holographic reconstruction is performed, can reveal important variations among different cell types such as a granulocyte vs. lymphocyte. This is also an important source of digital information that can potentially permit diagnosis of an infectious disease (such as malaria) based on e.g., inspection of the infected RBC hologram textures and detection of textural asymmetries against a library of healthy blood cells.

While the system 10, 50, 70 described herein is particularly suited for generating images of micro-objects another use of the invention is the automatic counting of micro-objects such as cells. The system 10, 50, 70 may count the total number of cells or even sub-population of cells from a larger population. The cell identification algorithm can be represented by a series of linear steps ultimately resulting in a properly counted image. To begin, a Laplacian-of-Gaussian (LoG) convolution filter is applied to the entire image. This is an important measure in enhancing cell locations from background noise as well as distinguishing any partially overlapping cells in samples of high density. Any problems from illumination gradients, thin film interference patterns, or pixel noise will be also be mitigated by the LoG filter. Once filtering is complete, points of interest can be extracted from the filtered image by means of a threshold operation whereby all pixel values below a certain value will be set to black and remaining pixels will be set to white, resulting in a binary black and white image. However, this introduces a problem where clusters of cells or cells in very close proximity may be joined in the binarization process. To address this problem, separation is achieved through the application of a watershed filter which will partition two connected objects at their point of minimum overlap. At this stage, one has successfully identified salient points of interest within the field-of-view. Such points are likely to represent target cell locations; however, a proper screening process is necessary to discriminate valid points from erroneous points. Toward this endeavor, a set of descriptors is applied to each potential cell location based on its size, circularity, signal to noise ratio, and local peak value in the LoG domain as well their holographic signatures in the recovered phase or measured amplitude domains. Any point that is not within a range of acceptable criteria based upon these parameters will be pruned from the set of valid count objects. With the finalization of the pruning process, markers are printed on the original image and statistical information about the counted cells is written to an XML file for further analysis if necessary.

Figure 13B:
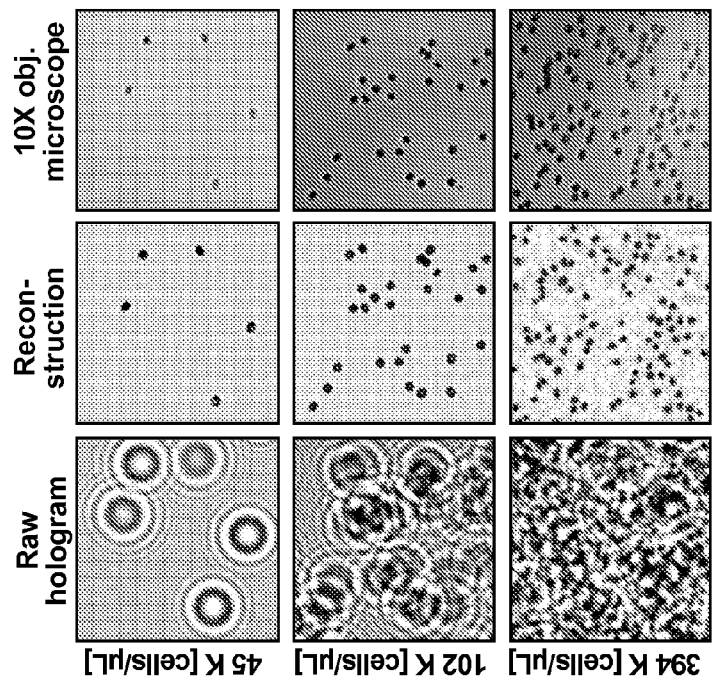
FIG. 13B illustrates the raw hologram and reconstruction images for various densities of cells along with the 10× microscope objective view.
Figure 13A:
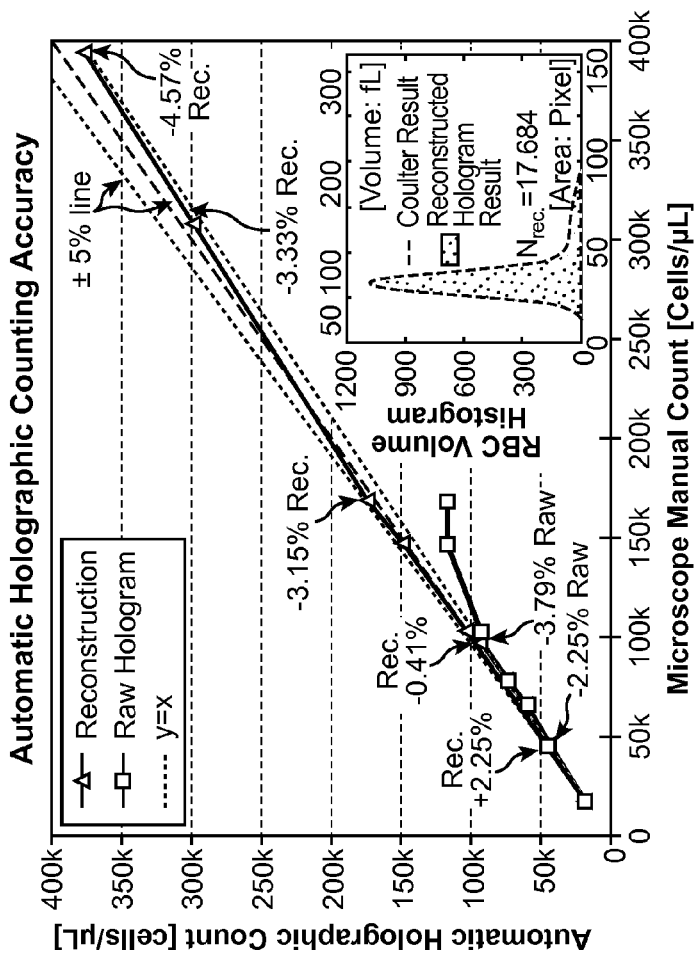
FIG. 13A illustrates a graph comparing the accuracy of a microscopic manual count of cells with the automatic holographic count.

FIG. 13A illustrates a graph comparing the accuracy of a microscopic manual count of cells with the automatic holographic count. The automated counting accuracy of the incoherent cell holography method is illustrated at various RBC densities ranging from <5,000 cells/µL up to 0.4 Million cells/µL. Using the 2D texture of raw cell holograms, an accurate cell count with <5% error rate can be achieved up to a density of ~100,000 cells/µL, whereas the reconstructed cell images yielded an error rate of <5% up to a cell density of ~400,000 cells/µL.

The inset in FIG. 13A also illustrates a comparison of RBC volume histogram that is estimated based on holographic reconstructions against a commercially available hematology analyzer (Coulter LH750, Beckman Coulter), which showed very good fit to the reported results. FIG. 13B illustrates the strength and accuracy of the holographic reconstruction process even for highly dense cell solutions.

As illustrated in FIG. 13A, error rates lower than 5% for samples of densities exceeding $3.5 \times 10^5$ cells/µL have been demonstrated for a variety of samples. Moreover, the algorithm scales well for very large images with high quantities of cells. A system 10, 50, 70 with modest hardware specifications can successfully count a sample with several thousand cells in an image of several megapixels in much less than a minute. For instance, a one megapixel image with ~5,000 cells can be counted in less than three seconds on a 2.5 GHz processor.

Figure 14:
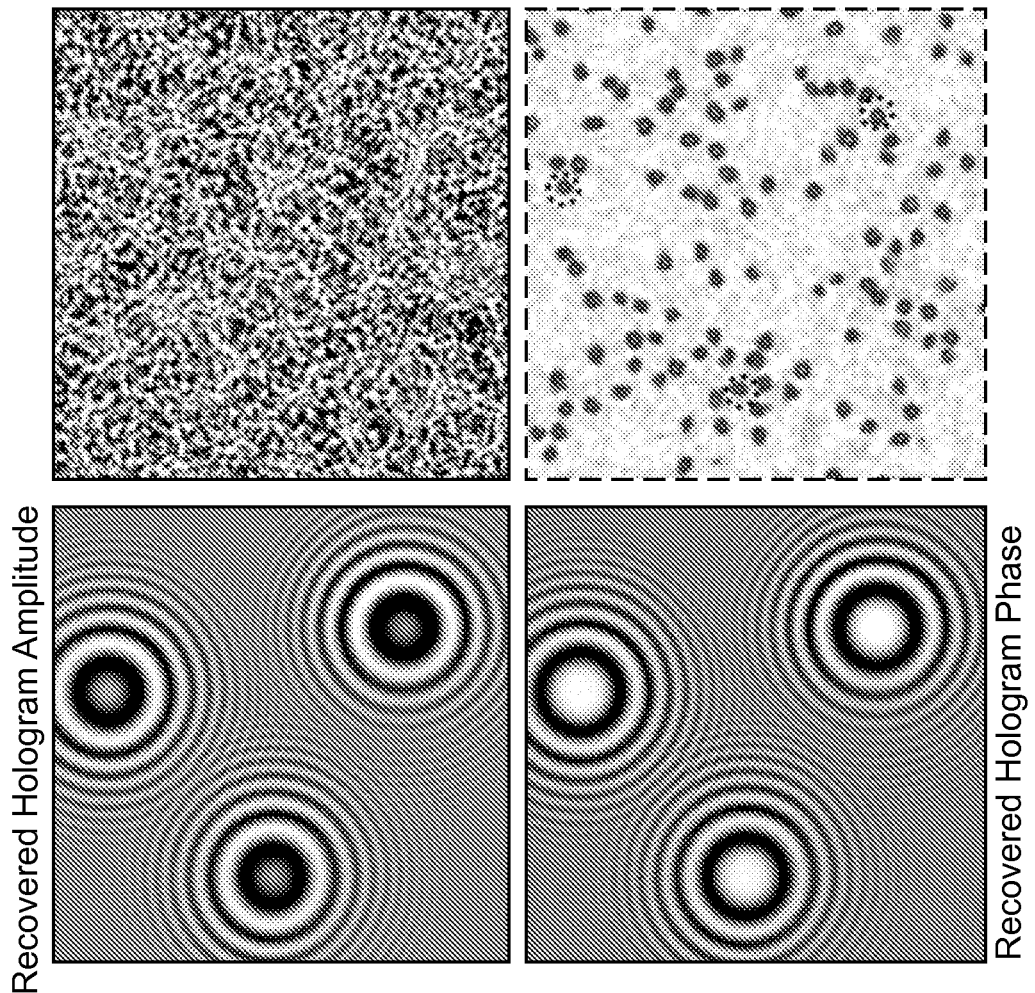
FIG. 14 illustrates images for RBCs at a density of 0.4 Million cells/µL. The top left image is the raw hologram plane where all the cell holograms overlap. The top right image shows the reconstructed cell images. The bottom images illustrate the isolated phase and amplitude holographic signatures of three selected RBCs that are shown within circles in the top right image.

The incoherent lensfree holography system 10, 50, 70 permits isolation of the individual hologram of any given cell within a cell hologram crowd. This is illustrated in FIG. 14 for three RBCs at a density of 0.4 Million cells/µL. The top left image is the raw hologram plane where all the cell holograms overlap. The top right image shows the reconstructed cell images. The bottom images illustrate the isolated phase and amplitude holographic signatures of three selected RBCs that are shown within circles in the top right image. This feature may especially be useful for making diagnostic decisions in a dense solution based on cell hologram texture asymmetries indicating the signature of a potential parasite such as malaria.

While the invention described herein has largely been described as a "lens free" imaging platform, it should be understood that various optical components, including lenses, may be combined or utilized in the systems and methods described herein. For instance, the devices described herein may use small lens arrays (e.g., micro-lens arrays) for non-imaging purposes. As one example, a lens array could be used to increase the efficiency of light collection for the sensor array. Such optical components, while not necessary to image the sample and provide useful data and results regarding the same may still be employed and fall within the scope of the invention.

While embodiments of the present invention have been shown and described, various modifications may be made without departing from the scope of the present invention. The invention, therefore, should not be limited, except to the following claims, and their equivalents.

What is claimed is:

1. A system for imaging a cytological sample comprising:
a sample holder configured to hold a cytological sample;
a spatial filter disposed at a distance $z_1$ from the sample holder on a first side of the sample holder, the spatial filter having an aperture disposed therein configured to allow the passage of illumination;
an image sensor array disposed at a distance $z_2$ from the sample holder on a second, opposite side of the sample holder, wherein $z_1 \ll z_2$;
an illumination source configured to illuminate the cytological sample through the aperture, the spatial filter being interposed between the illumination source and the sample holder; and
at least one processor configured to receive image frames from the imaging sensor array containing raw holographic images of objects of interest in the cytological sample and further configured to recover a lost hologram phase of the objects of interest and reconstruct a complex image of the objects of interest.

2. The system of claim 1, wherein $z_1$ is in the range of about 1 cm to about 10 cm and $z_2$ is in the range of about 0.05 mm to about 2 cm.

3. The system of claim 1, wherein the sample holder is disposed in a mobile phone and configured to hold a cytological sample, the mobile phone dimensioned for hand-held portability.

4. The system of claim 3, wherein the mobile phone is configured for wireless transmission of data.

5. The system of claim 1, wherein the sample holder is disposed in a personal digital assistant.

6. The system of claim 4, wherein the spatial filter and the illumination source are contained with a housing configured to be removable from the mobile phone and the imaging sensor is disposed in the mobile phone.

7. The system of claim 1, wherein the sample holder comprises a microfluidic device.

8. The system of claim 1, further comprising:
a prism interposed between the spatial filter and the sample holder;
a fluorescent illumination source configured to illuminate the cytological sample through the prism, wherein substantially all of the incident fluorescent illumination is reflected through total internal reflection (TIR).

9. The system of claim 8, further comprising an optical filter interposed between the sample holder and the imaging sensor array.

10. The system of claim 9, further comprising an optic-faceplate comprising a plurality of fiber optic fibers interposed between the prism and the imaging sensor array.

11. The system of claim 1, wherein the imaging sensor array is contained in a portable electronic device and the illumination source is disposed within an extension configured to be secured to the portable electronic device adjacent to the imaging sensor array.

12. The system of claim 1, wherein the sample holder and the imaging sensor are disposed in a mobile communications device.

13. A method of imaging a cytological sample comprising:
illuminating a front side of a sample holder configured to hold a cytological sample with an illumination source emitting at least partially incoherent light, the at least partially incoherent light passing through an aperture prior to illuminating the cytological sample, wherein the aperture is disposed at a distance $z_1$ from the sample holder and the imaging sensor array is disposed at a distance $z_2$ from an opposing side of the sample holder wherein $z_2 \ll z_1$;
obtaining one or more image frames from an imaging sensor array disposed on a back side of the sample holder, the one or more image frames containing raw holographic images of objects of interest within the cytological sample;
processing the one or more image frames containing raw holographic images of objects of interest with a processor to recover lost hologram phase information of the objects of interest contained within the image frames;
outputting from the processor a reconstructed image of the objects of interest based at least in part on the raw holographic images and the lost hologram phase information.

14. The method of claim 13, wherein the at least one processor compares one or more image frames with a library and, at least in part based on said comparison, identifies one or more cells, organelles, particles contained in the sample.

15. The method of claim 13, wherein the at least one processor outputs a cell count.

* * * * *